United States Patent
He

(10) Patent No.: US 8,349,998 B2
(45) Date of Patent: *Jan. 8, 2013

(54) FUSED THIOPHENES, METHODS FOR MAKING FUSED THIOPHENES, AND USES THEREOF

(75) Inventor: Mingqian He, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/907,453

(22) Filed: Oct. 19, 2010

(65) Prior Publication Data

US 2011/0040042 A1 Feb. 17, 2011

Related U.S. Application Data

(62) Division of application No. 12/561,760, filed on Sep. 17, 2009, now Pat. No. 7,893,191, which is a division of application No. 11/661,732, filed on Feb. 28, 2007, now Pat. No. 7,705,108.

(60) Provisional application No. 60/609,881, filed on Sep. 14, 2004.

(51) Int. Cl.
*C08G 75/00* (2006.01)

(52) U.S. Cl. .......... 528/377; 528/380; 528/226; 549/11; 549/17; 549/49

(58) Field of Classification Search .............. 549/11, 549/17, 49; 528/377, 380
See application file for complete search history.

(56) References Cited

U.S. PATENT DOCUMENTS

| 6,403,809 B1 | 6/2002 | Holmes et al. .................. 549/41 |
| 6,645,401 B2 | 11/2003 | Giles et al. ..................... 252/500 |
| 6,800,763 B2 | 10/2004 | Farrand et al. .................. 549/50 |
| 6,818,260 B2 | 11/2004 | Farrand et al. .................. 428/1.1 |
| 2004/0127592 A1 | 7/2004 | Heeney et al. .................... 522/6 |
| 2004/0230021 A1 | 11/2004 | Giles et al. ....................... 528/4 |

FOREIGN PATENT DOCUMENTS

| EP | 0592919 | 4/1994 |
| EP | 1275650 | 1/2003 |
| EP | 1275651 | 1/2003 |
| EP | 1284276 | 2/2003 |
| EP | 1477504 | 11/2004 |
| EP | 1510535 | 3/2005 |
| WO | 97-35858 | 10/1997 |
| WO | 99-12989 | 3/1999 |
| WO | 2005-111045 | 11/2005 |
| WO | 2005-121150 | 12/2005 |
| WO | 2006-021277 | 3/2006 |

OTHER PUBLICATIONS

Barbarella et al., "Rigid-Core Oligothiophene-S,S-dioxides with High Photoluminescence Efficencies Both in Solution and in the Solid State," Chem. Mater 2001, 13, 4112-4122, published online on Sep. 25, 2001.

(Continued)

*Primary Examiner* — Shane Fang
(74) *Attorney, Agent, or Firm* — Jason A. Barron; Kevin M. Able; Siwen Chen

(57) ABSTRACT

Described herein are compositions including heterocyclic organic compounds such as fused thiophene compounds, methods for making them, and uses thereof.

12 Claims, 12 Drawing Sheets

R = alkyl group having at least 4 carbons
Z = terminus of carboxylate

OTHER PUBLICATIONS

Tedesco et al., "Solid-State Supramolecular Organization, Established Directly from Powder Diffraction Data, and Photoluminescence Efficiency of Rigid-Core Oligothiophene-S,S-dioxides," J.Am.Chem Soc. 2003, 125, 12277-12283,published online on Sep. 17, 2003.

Catellani et al., "Dithienothiophene and dithienothiophene-S,S-dioxide copolymers for photovoltaics," Thin Solid Films 2002, 403-404, 66-70.

Sotgiu et al., "Rigid-Core Fluorescent Oligothiophene-S,S-dioxide Isothiocyanates. Synthesis, Optical Characterization, and Conjugation to Monoclonal Antibodies," J. Org. Chem. 2003, 68, 1512-1520.

Zhang et al., "Alkyl-Substituted Thieno [3,2-b] thiophene Polymers and Their Dimeric Subunits," Macromolecules 2004, 37, 6306-6315, published online on Jul. 30, 2004.

Zhang et al., "Synthesis and Structure of Fused Oligothiophenes with up to Seven Rings,"J.Am. Chem. Soc. 2005, 127, 10502-10503, published online on Jul. 7, 2005.

Inaoka and Collard, "Synthesis, polymerization and characterization of substituted dithieno [3,4-b:3',4'-d] thiophenes," J. Mater. Chem., 1999, 9, 1719-1725.

Diez et al., "Synthesis of a Thienothiophene Conjugated Polymer", Molecules, vol. 5, 2000, pp. 555-556.

Dimitrakopoulos et al., "Organic Thin Film Transistors for Large Area Electronics", Advanced Materials, vol. 14, No. 2, Jan. 16, 2002, pp. 99-117.

Ostroukhova et al., "High-Temperature Organic Synthesis", Journal of Organic Chemistry USSR, 1991, pp. 301-305.

Laquindanum et al., "Morphological Origin of High Mobility in Pentacene Thin-Film Transistors", Chem. Mater., vol. 8, 1996, pp. 2542-2544.

Andersson et al., "Regioselective Polymerization of 3-(4-Octylphenyl)thiophene with $FeCl_3$", Macromolecules, vol. 27, 1994, pp. 6503-6506.

Dejong and Janssen, "The Synthesis, Oxidation and Electronic Spectra of Four Dithienothiophenes," Org. Chem., 1971, vol. 36, No. 12, 1645-1648.

Choi et al., "A One-Pot Synthesis of Substituted Thieno [3,2-b] Thiophenes and Selenolo [3,2-b] Selenophenes," Heterocycles,1994, vol. 38, No. 1, 143-149.

Ostroukhova et al. "Thermal Reactions of DI (1-Propenyl) Sulfide," Zhurnal Orgenicheskoi Khimii vol. 27, No. 2, pp. 354-359, Feb. 1991. (Translation).

Chantson et al. "Insertion of Pt into C-H and C-S bonds of thiophene derivatives. The X-ray crystal structure of a thiaplatinacycle of 3,6-dimethylthieno[3,2-b] thiopene," Journal of Organometallic Chemistry, 687 (2003) 39-45.

Oyaizu et al., "Linear Ladder-Type pi-Conjugated Polymers Composed of Fused Thiophene Ring Systems," Macromolecules 2004, 37, 1257-1270.

Kraft et al., "Electroluminescent Conjugated Polymers—Seeing Polymers in a New Light," Angew. Chem. Int. Ed. 1998, 37, 402-428.

Barbarella et al., "Rigid-Core Oligothiophene-S,S-dioxides with High Photoluminescence Efficencies Both in Solution and in the Solid State," Chem. Mater 2001, 13 (11) 4111-4115.

R = alkyl group having at least 4 carbons
Z = terminus of carboxylate

R = alkyl group having at least 4 carbons
Z = terminus of carboxylate

R = alkyl group having at least 4 carbons
Z = terminus of carboxylate

R = alkyl group having at lesat 4 carbons

FUSED THIOPHENES, METHODS FOR MAKING FUSED THIOPHENES, AND USES THEREOF

CROSS-REFERENCE TO RELATED APPLICATION

This application is a divisional application of U.S. patent application Ser. No. 12/561,760 filed on Sep. 17, 2009 now U.S. Pat. No. 7,893,191 and entitled "FUSED THIOPHENES, METHODS FOR MAKING FUSED THIOPHENES, AND USES THEREOF," which, in turn, is a divisional application of U.S. patent application Ser. No. 11/661,732 filed on Feb. 28, 2007 now U.S. Pat. No. 7,705,108 and entitled "FUSED THIOPHENES, METHODS FOR MAKING FUSED THIOPHENES, AND USES THEREOF," which, in turn, claims the benefit of U.S. Provisional Application Ser. No. 60/609,881 filed on Sep. 14, 2004 and entitled "Fused Thiopenes And Methods For Making Fused Thiophenes," the contents of all of which are relied upon and incorporated herein by reference in their entirety.

BACKGROUND

1. Field of the Invention

Described herein are compositions including heterocyclic organic compounds. More specifically, described herein are fused thiophene compounds, methods for making them, and uses thereof.

2. Technical Background

Highly conjugated organic materials are currently the focus of great research activity, chiefly due to their interesting electronic and optoelectronic properties. They are being investigated for use in a variety of applications, including field effect transistors (FETs), thin-film transistors (TFTs), organic light-emitting diodes (OLEDs), electro-optic (EO) applications, as conductive materials, as two photon mixing materials, as organic semiconductors, and as non-linear optical (NLO) materials. Highly conjugated organic materials may find utility in devices such as RFID tags, electroluminescent devices in flat panel displays, and in photovoltaic and sensor devices.

Materials such as pentacene, poly(thiophene), poly(thiophene-co-vinylene), poly(p-phenylene-co-vinylene) and oligo(3-hexylthiophene) have been intensively studied for use in various electronic and optoelectronic applications. More recently, fused thiophene compounds have been found to have advantageous properties. For example, bisdithieno[3,2-b:2',3'-d]thiophene (1, j=2) has been found to efficiently π-stack in the solid state, possesses high mobility (up to 0.05 cm$^2$/V·s), and has a high on/off ratio (up to 10$^8$). Oligomers and polymers of fused thiophenes, such as oligo- or poly(thieno[3,2-b]thiophene (2) and oligo- or poly(dithieno[3,2-b:2'-3'-d]thiophene)(1)

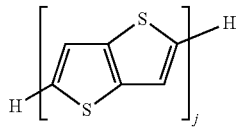

1

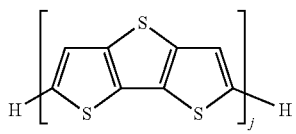

2 have also been suggested for use in electronic and optoelectronic devices, and have been shown to have acceptable conductivities and non-linear optical properties. Unsubstituted fused thiophene-based materials tend to suffer from low solubility, marginal processability and oxidative instability. Thus, there remains a need for fused thiophene-based materials having acceptable solubility, processability and oxidative stability.

SUMMARY

Described herein are compositions including heterocyclic organic compounds such as fused thiophene compounds, methods for making them, and uses thereof. The compositions and methods described herein possess a number of advantages over prior art compositions and methods. For example, the fused thiophene compositions described herein can be made to be more soluble and processable than the analogous unsubstituted thiophene compositions. Polymers and oligomers including the fused thiophene moieties described herein can be made to be processable using conventional spin-coating operations. Further, the compositions described herein can be made with substantially no β-H content, greatly improving the oxidative stability of the compositions.

Additional features and advantages will be set forth in the detailed description which follows, and in part will be readily apparent to those skilled in the art from the description or recognized by practicing the invention as described in the written description and claims hereof, as well as in the appended drawings.

It is to be understood that both the foregoing general description and the following detailed description are merely exemplary, and are intended to provide an overview or framework for understanding the nature and character of the invention.

BRIEF DESCRIPTION OF THE DRAWINGS

The accompanying drawings are included to provide a further understanding of the invention, and are incorporated in and constitute a part of this specification. The drawings are not necessarily to scale, and sizes of various elements may be distorted for clarity. For example, for the sake of clarity, not all distal ends of the optical fibers are shown in the drawings. The drawings illustrate one or more embodiment(s) of the invention and together with the description serve to explain the principles and operation of the invention.

DETAILED DESCRIPTION

Figure 1:
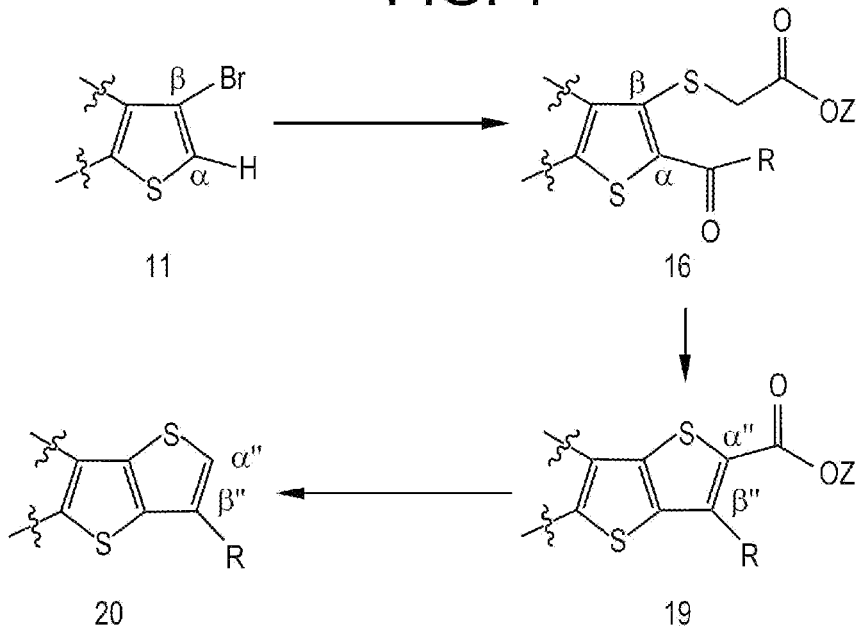
FIG. 1 is a reaction scheme showing a method for making a β"-R-substituted fused thiophene moieties.

Before the present materials, articles, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

The term "alkyl group" as used herein is a branched or unbranched saturated hydrocarbon group of 1 to 40 carbon atoms, such as methyl, ethyl, n-propyl, isopropyl, n-butyl, isobutyl, t-butyl, pentyl, hexyl, heptyl, octyl, decyl, or tetradecyl, and the like. The term "unsubstituted alkyl group" is defined herein as an alkyl group composed of just carbon and hydrogen. The term "substituted alkyl group" is defined herein as an alkyl group with one or more hydrogen atoms substituted with a group including, but not limited to, an aryl group, cycloalkyl group, aralkyl group, an alkenyl group, an alkynyl group, an amino group, an ester, an aldehyde, a hydroxyl group, an alkoxy group, a thiol group, a thioalkyl group, or a halide, an acyl halide, an acrylate, or a vinyl ether.

The term "alkyl group" as defined herein also includes cycloalkyl groups. The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term cycloalkyl group also includes a heterocycloalkyl group, where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aryl group" also includes "heteroaryl group," which is defined as an aryl group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "aralkyl" as used herein is an aryl group having an alkyl group as defined above attached to the aryl group. An example of an aralkyl group is a benzyl group.

The term "alkenyl group" is defined as a branched or unbranched hydrocarbon group of 2 to 40 carbon atoms and structural formula containing at least one carbon-carbon double bond.

The term "alkynyl group" is defined as a branched or unbranched hydrocarbon group of 2 to 40 carbon atoms and a structural formula containing at least one carbon-carbon triple bond.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

In one aspect, described herein are compositions comprising at least one fused thiophene moiety comprising the formula 3 or 4

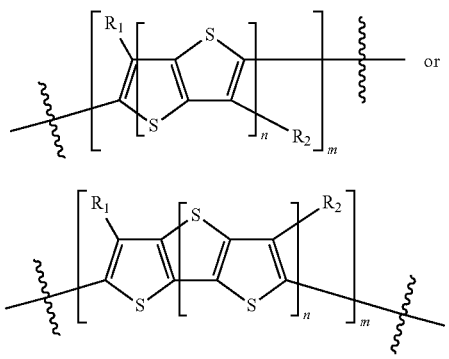

In one aspect, with respect to structures 3 and 4, n is an integer greater than zero; m is no less than one; $R_1$ and $R_2$ are, independently, hydrogen or an alkyl group, wherein at least one of $R_1$ and $R_2$ is an alkyl group, and wherein when the fused thiophene moiety has the formula 4, n is not 1. As used herein, the fused thiophene ring system of a fused thiophene moiety is the heterocyclic core of the moiety, and does not include the α-substituents and the β-substituents (e.g. $R_1$ and $R_2$) bound to the fused thiophene ring system. For example, the fused thiophene ring systems of structures 3 and 4 having n=1 are shown below as structures 5 and 6, respectively.

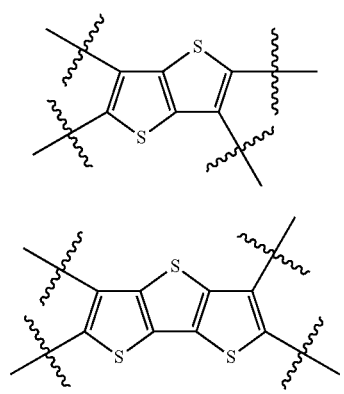

The fused thiophene moieties described herein can have any number of fused rings. For example, the fused thiophene moieties can be bicyclic (3, n=1); tricyclic (4, n=1); tetracyclic (3, n=2); pentacyclic (4, n=2), hexacyclic (3, n=3); or heptacyclic (4, n=3). The methods described herein permit the construction of fused thiophene moieties having any desired number of rings. In one aspect, n is 1, 2, 3, 4, 5, 6, 7, 8, 9, 10, 11, 12, 13, 14, or 15. In other aspects, the fused thiophene moiety can be tricyclic or greater (i.e., 4, n≦1; or 3, n≦2).

The fused thiophene moieties described herein are substituted at least one of the β-positions of the fused thiophene ring system with an alkyl group. As used herein, an α-position of a fused thiophene ring system is a non-fused carbon center that is directly adjacent to the sulfur of a fused thiophene, while a β-position is a non-fused carbon center that is separated from the sulfur of the fused thiophene by an α-position. In the structures 3 and 4, the α-positions are shown as being connected to the rest of the composition, while the β-positions are substituted with $R_1$ and $R_2$.

In one aspect, at least one of $R_1$ and $R_2$ is an alkyl group. Previously, there have been no methods for producing fused thiophene moieties of structures 3 and 4 having alkyl substitution at the β-positions of the fused thiophene ring system. As described in more detail in the Examples, below, methods conventionally used to alkylate simple unfused thiophenes fail when used in attempts to alkylate fused thiophene ring systems. In one aspect, described herein are methods for making fused thiophene moieties having large alkyl substitution at the β-positions of the fused thiophene ring system.

In one aspect, $R_1$ and $R_2$ can be a variety of substituted or unsubstituted alkyl groups. For example, at least one of $R_1$ or $R_2$ is an unsubstituted alkyl group. In this aspect, the unsubstituted alkyl group can be a straight-chain alkyl group (e.g. methyl, ethyl, propyl, butyl, pentyl, hexyl, heptyl, octyl, nonyl, decyl, undecyl, dodecyl or hexadecyl), a branched alkyl group (e.g. sec-butyl, neo-pentyl, 4-methylpentyl), or a substituted or unsubstituted cycloalkyl group (e.g. cyclopentyl, cyclohexyl). In another aspect, at least one of $R_1$ or $R_2$ is an alkyl group, itself at least four carbons in size, which is substituted. In a further aspect, substitution of the alkyl group is separated from the fused thiophene ring system by at least two carbons. In one aspect, $R_1$ and/or $R_2$ can be substituted with an aryl group, cycloalkyl group, aralkyl group, an alkenyl group, an alkynyl group, an amino group, an ester, an aldehyde, a hydroxyl group, an alkoxy group, a thiol group, a thioalkyl group, or a halide, acyl halide, an acrylate, or a vinyl ether. Examples of substituted alkyl groups include, but are not limited to, 6-hydroxyhexyl and 3-phenylbutyl. The selection of $R_1$ and $R_2$ will depend on the end use of the fused thiophene moiety-containing composition. The methods described herein permit the synthesis of fused thiophene moieties having a wide variety of $R_1$ and $R_2$ substituents. Any functionality on a substituted alkyl group can be protected in order to survive subsequent reaction steps.

Unsubstituted fused thiophene ring systems (i.e., no substitution at the α- or β-positions) tend to be relatively insoluble. Thus, in one aspect, $R_1$ and $R_2$ can be an alkyl group having at least six carbons in size. For example, the alkyl group can have the formula $C_kH_{2k-1}$, where k is an integer greater than or equal to six.

In certain aspects, the fused thiophene ring system is substituted at both β-positions, so that there are no β-hydrogens on the ring system. For example, in one aspect, neither $R_1$ nor $R_2$ in structures 3 and 4 is H. Such moieties can be incorporated in oligomers and polymers having substantially no β-hydrogen content, and will have increased oxidative stability. For example, the molar ratio of β-hydrogen to fused thiophene ring system can be less than about ⅙, 1/7, ⅛, 1/9, or 1/10. In a further aspect, one or both of $R_1$ and $R_2$ can be an alkyl group. In one aspect, $R_1$ and $R_2$ are the same alkyl group. In one aspect, $R_1$ and $R_2$ are identical alkyl groups. When $R_1$ and $R_2$ are identical, regioregular polymers can be easily constructed because the problems of regioselectivity (i.e. head-to-tail vs. head-to-head coupling) of polymerization reactions disappear. In other aspects, $R_1$ and $R_2$ may also be different. For example, $R_1$ can be at least four carbons in size, with $R_2$ being less than four carbons in size (e.g., a methyl group). Alternatively, in another aspect, both $R^1$ and $R^2$ can be at least four carbons in size.

The fused thiophene moieties of structures 3 and 4 can exist as simple monomeric fused thiophenes, or can be incorporated into more complex compounds, oligomers or polymers. For example, the fused thiophene moieties described herein can be incorporated in simple fused thiophene monomers having the formulae 7 and 8,

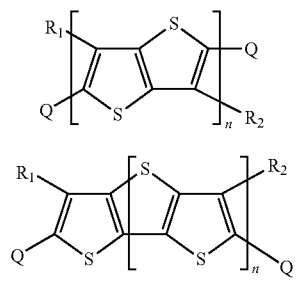

wherein n is an integer greater than zero; $R_1$ and $R_2$ are, independently, hydrogen or an alkyl group, and Q is, independently, hydrogen, an alkyl group, an acyl halide, an ester, an aldehyde, a ketone, a hydroxyl group, a thiol group or alkyl substituted thiol group, an alkoxy group, an acrylate group, an amino group, a vinyl ether, or a halide. In certain aspects, monomers having structures 7 and 8 can be used to make fused thiophene oligomers and polymers, as described below.

The fused thiophene monomers 7 and 8 can be incorporated in oligomers and polymers having conjugated homo-oligomeric or homopolymeric blocks of the fused thiophene moieties to produce polymers having the fused thiophene moieties 3 and 4. For example, according to one embodiment, an oligomer or polymer includes a fused thiophene of structure 3 or 4 in which m is greater than 1. In further embodiments, m is at least about four. In another aspect, when the polymer is a homopolymer, m is at least about 10. In this aspect, it is contemplated that the monomers 7 or 8 can be polymerized to produce a homopolymer composed of residues having the formula 3 and/or 4. In other aspects, m is from 1 to 10,000, 1, to 9,000, 1 to 8,000, 1 to 7,000, 1 to 6,000, 1 to 5,000, 1 to 4,000, 1 to 3,000, 1 to 2,000, 1 to 1,000, 1 to 500, 1 to 250, 1 to 100, 1 to 50, 1 to 25, or 1 to 10.

In other aspects, the fused thiophene monomers described herein (e.g., 7 and 8) can be incorporated into conjugated copolymers with other aromatic or unsaturated moieties. For example, the fused thiophene monomers 7 and 8 can be copolymerized with other substituted or unsubstituted fused thiophene moieties to form a conjugated fused thiophene polymer or oligomer. Alternatively, the fused thiophene monomers 7 and 8 can be copolymerized with substituted or unsubstituted thiophenes to form thiophene/fused thiophene polymers or oligomers. The fused thiophene monomers 7 and 8 can also be copolymerized with other moieties commonly used in conjugated polymers, such as vinylene, phenylene, or other arylene or heteroarylene moieties.

The fused thiophene moieties described herein can be incorporated into a wide variety of other types of polymers. For example, the fused thiophenes having the formula 7 and 8 can be incorporated into the main chain of a polymer such as, for example, a polyester, a polyurethane, a polyamide, or a polyketone; and in the side chain of a polymer such, for example, a polyacrylate, a polymethacrylate, or a poly(vinyl ether). It is contemplated that the fused thiophenes having the formula 7 and 8 can be modified with reactive groups (e.g., acyl chloride, alcohol, acrylate, amine, vinyl ether) that will permit the incorporation of the monomer into the polymer. For example, $R^1$, $R^2$, and/or Q can be modified with such reactive groups.

In another aspect, the fused thiophenes described herein can also be incorporated in donor-acceptor chromophores, such as those commonly used in polymeric electro-optic materials. For example, the fused thiophene moieties of structures 3 and 4 can be incorporated into a donor-acceptor chromophore having the structure 9 or 10:

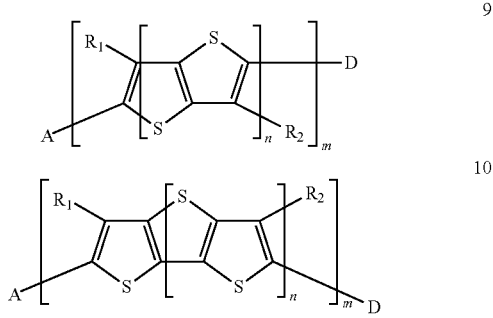

where D is an electron donating group, and A is an electron accepting group. Donor-acceptor chromophores are described in more detail in U.S. Pat. Nos. 6,584,266; 6,514,434; 6,448,416; 6,444,830; and 6,393,190, each of which is hereby incorporated herein by reference in its entirety. In one aspect, the fused thiophene having the formula 7 or 8 can be reacted with an electron donating group and electron accepting group to produce compounds having the formula 9 and 10, respectively.

In various aspects, the compositions described herein have a sufficiently high concentration of the fused thiophene moieties of structures 3 or 4 to yield a desired electronic or optoelectronic property to the composition. For example, the compositions have at least one fused thiophene moiety of structures 3 or 4 in a total concentration of at least 1 wt %. In a further aspect, the compositions described herein have at least one fused thiophene moiety of structures 3 or 4 in a total concentration of at least 3 wt %. In additional aspects, the composition has at least one fused thiophene moiety of structures 3 or 4 in higher total concentrations of, for example, at least 10 wt % or at least 50 wt %. Due to the presence of an alkyl group at the β-position of the fused thiophene ring, the compositions can have higher concentrations of fused thiophene moieties yet remain soluble and processable.

The compositions described herein (monomers, oligomers, polymers) can be used to make a wide variety of devices. For example, the device can be a fused thiophene moiety-containing composition configured in an electronic, optoelectronic, or nonlinear optical device. The compositions described herein can also be used in field effect transistors (FETs), thin-film transistors (TFTs), organic light-emitting diodes (OLEDs), electro-optic (EO) applications, as conductive materials, as two photon mixing materials, as organic semiconductors, as non-linear optical (NLO) materials, as RFID tags, as electroluminescent devices in flat panel displays, and in photovoltaic and sensor devices.

Described herein are methods for making fused thiophene compounds. In one aspect, the method for making a β"-R-substituted fused thiophene moiety comprises the steps of:
(i) providing an α-hydro β-bromo thiophene moiety;
(ii) converting the α-hydro β-bromo thiophene moiety to an α-(R-acyl)-β-carboxymethylthio thiophene moiety by acylating the thiophene moiety at the α-position with an R-acyl moiety, where R is an alkyl group having at least four carbons,
(iii) substituting the β-bromide with a 2-mercaptoacetate;
(iv) cyclizing the α-(R-acyl)-β-carboxymethylthio thiophene moiety to form an α"-carboxy-β"-R-substituted fused thiophene moiety; and
(v) decarboxylating the α"-carboxy β"-R-substituted fused thiophene moiety to form the β"-R-substituted fused thiophene moiety.

In one aspect, a method for making a β"-R-substituted fused thiophene compound is shown in the reaction scheme of FIG. 1. First, an α-hydro-β-bromo thiophene moiety 11 is provided. The α-hydro-β-bromo thiophene moiety 11 can be a simple unfused thiophene, as shown in structures 12 and 13 below. Structure 12 is an unsubstituted unfused α-hydro-β-bromo thiophene, which upon ring fusion produce thienothiophene 14 having a single βsubstitution. Structure 13 is R' substituted at the β' center (i.e., a α-hydro-β-bromo-β'-R'-substituted thiophene), which upon ring fusion produces a doubly β-substituted thienothiopene 15.

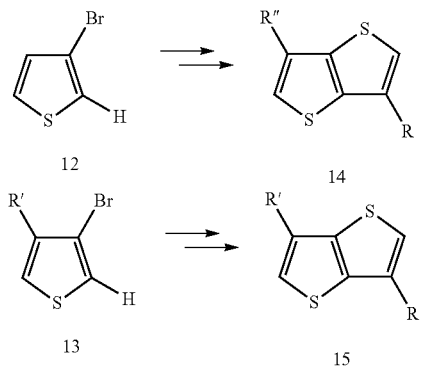

The α-hydro-β-bromo thiophene moiety is then converted to an α-(R-acyl)-β-carboxymethylthio thiophene moiety 16. As used herein, the name "R-acyl" is meant to denote radical structure 17 below, and the name "carboxymethylthio" is meant to denote radical structure 18 below, where Z is the terminus of the carboxylate (which may be, e.g., H, substituted alkyl, unsubstituted alkyl). In one aspect, Z is H, methyl, ethyl or propyl. The reaction scheme shown in FIG. 2 and described in more detail in the examples can be used to effect the conversion of the α-hydro-β-bromo thiophene moiety 11 to the α-(R-acyl)-β-carboxymethylthio thiophene moiety 16. The α-hydro-β-bromo thiophene moiety is first acylated at the α-position with a R-acyl moiety using RCOCl and AlCl₃, where R is an alkyl group having at least four carbons. The acylated product is reacted with the 2-mercaptoacetate HSCH₂COOZ to yield the α-(R-acyl)-β-carboxymethylthio thiophene moiety 16. While in the reaction scheme of FIG. 2, the R-acylation is performed first, in certain cases the reactions can be performed in the opposite order.

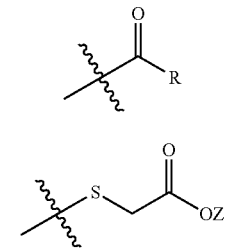

The α-(R-acyl)-β-carboxymethylthio thiophene moiety 16 is then cyclized (e.g., via a base-catalyzed condensation, often under the same conditions as the reaction with the 2-mercaptoacetate) to yield an α"-carboxy-β"-R-substituted fused thiophene moiety 19, which is decarboxylated to form the β"-R-substituted fused thiophene moiety 20, where R is an alkyl group having at least four carbons.

Figure 2:
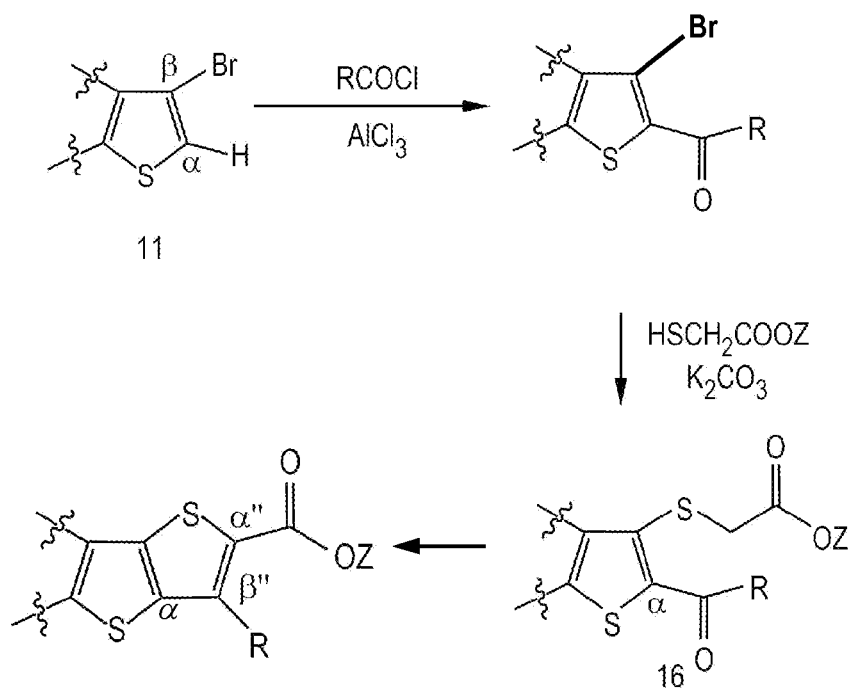
FIG. 2 is a reaction scheme showing a method for making an α-(R-acyl)-β-carboxymethylthio thiophene moiety.

If the α-hydro-β-bromo thiophene moiety 11 of the reaction scheme of FIG. 2 has a hydrogen at its α'-position, then the acylation step may not be specific to the α-position. For example, as shown in the reaction scheme of FIG. 3, α,α'-dihydro-β-bromo thiophene moiety 21 is acylated and reacted with a 2-mercaptoacetate, forming a mixture of products including the desired α-(R-acyl)-α'-hydro-β-carboxymethylthio thiophene moiety 22, as well as the undesired regioisomeric α'-hydro-α-(R-acyl)-β-carboxymethylthio thiophene moiety 23. Since moieties 22 and 23 are likely to be separable from one another, the cyclization step on the mixture can be performed; regioisomer 22 will cyclize to form α'-hydro-α"-carboxy-β"-R-substituted fused thiophene moiety 24, while regioisomer 23 will not cyclize. The fused thiophene moiety 24 can now be separated from uncylclized regioisomer 23, and can be decarboxylated to yield α'-hydro-β"-R-substituted fused thiophene moiety 25.

Figure 3:
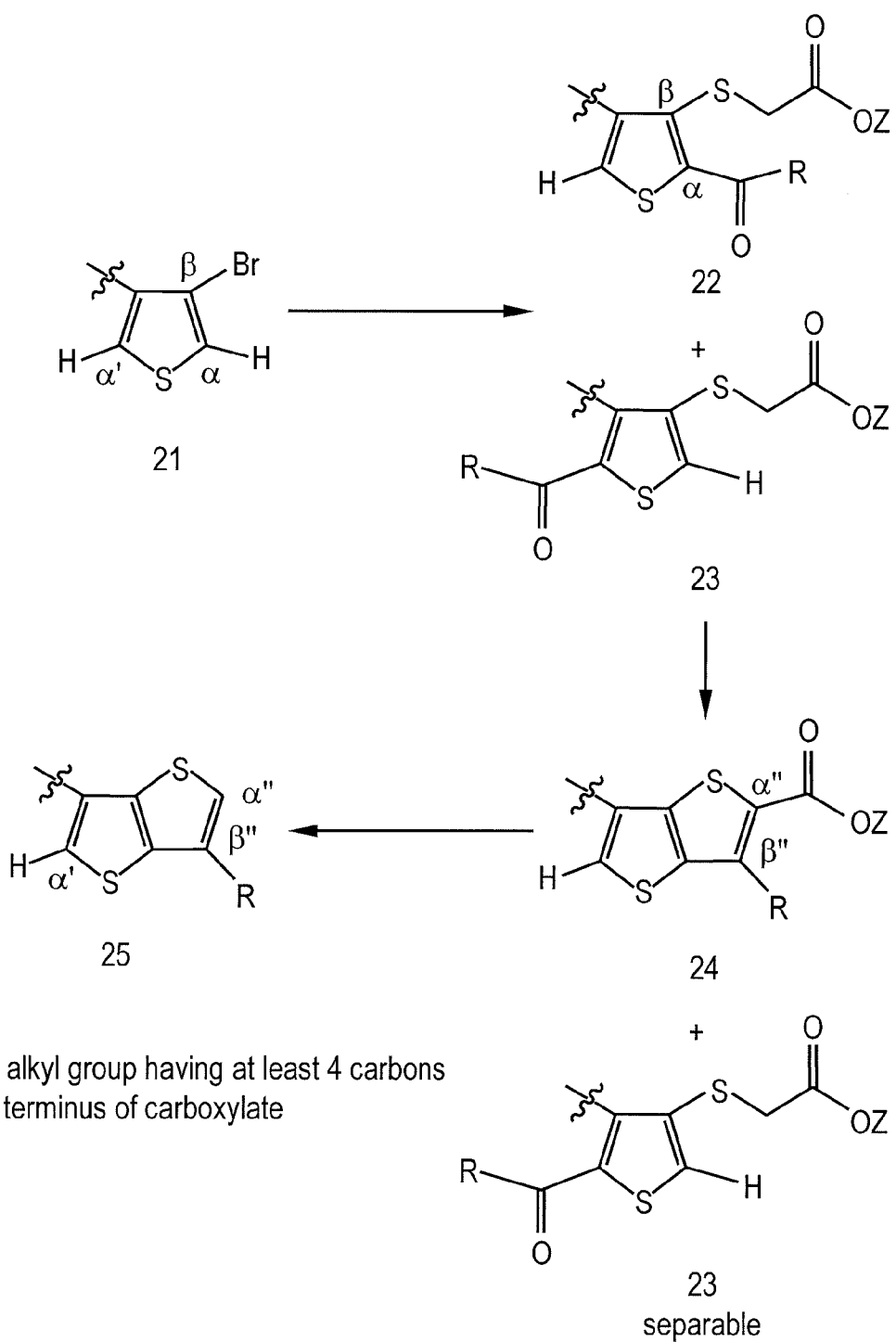
FIG. 3 is a reaction scheme showing a method for making an α'-hydro-β"-R-substituted fused thiophene moiety.

In other aspects, the methods described in the reaction schemes of FIGS. 2 and 3 can be used to make a variety of fused thiophene compounds. For example, if the α-hydro-β-bromo thiophene moiety 11 of the reaction scheme of FIG. 2 is an α-hydro-β-bromo-β'-R'-substituted thiophene moiety 13, then the end product fused thiophene will be a β"-R-substituted-β'-R'-substituted fused thiophene moiety 15. R' can be, for example, an alkyl group having at least four carbons, and can be the same as or different from R. R' can also be any other desired substitution, including an alkyl group having less than four carbons.

Figure 4:
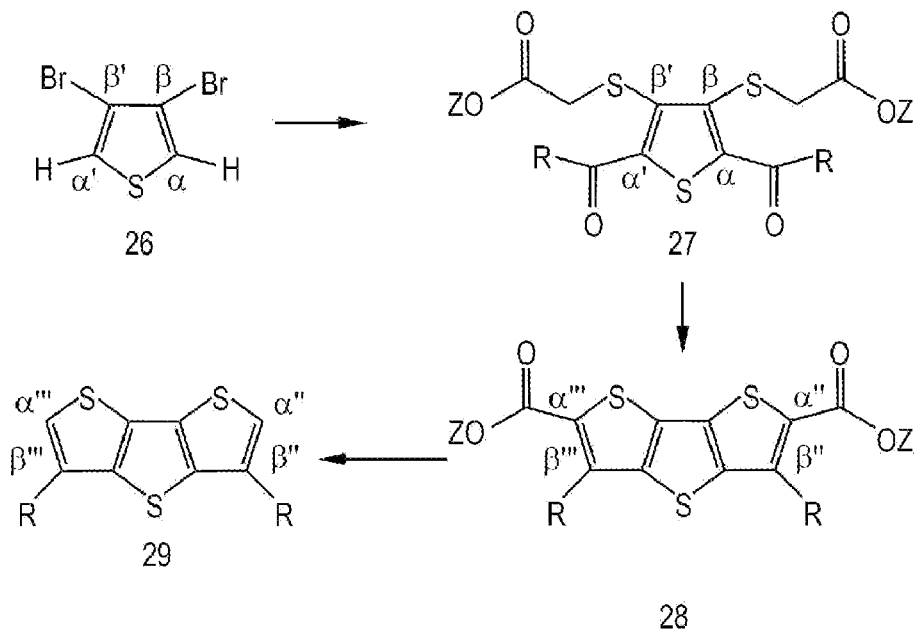
FIG. 4 is a reaction scheme in which there is a simultaneous cyclization on both sides of a thiophene moiety.

The general cyclization method of the reaction scheme of FIG. 2 can be used to simultaneously perform cyclization on both sides of a thiophene moiety, as shown in the reaction scheme of FIG. 4. An α,α'-dihydro-β,β'-dibromo thiophene moiety 26 is used as the starting material. While in the reaction scheme of FIG. 4 the α,α'-dihydro-β,β'-dibromo thiophene moiety 26 is shown as a monocyclic simple thiophene, the skilled artisan will understand that thiophene moiety 26 can have fused thiophenes (such as thieno[3,2-b]thiophene or bisdithieno[3,2-b:2'-3'-d]thiophene) as its fused thiophene ring system. Thiophene moiety 26 is acylated (for example, as described above using Friedel-Crafts chemistry) at both the α and α' positions, and is reacted with a 2-mercaptoacetate at both the β and β' positions to yield an α,α'-bis(R-acyl)-β,β'-bis(carboxymethylthio) thiophene moiety 27, which is cyclized (forming 28) and decarboxylated to form β'',β'''-bis(R-substituted) fused thiophene moiety 29, which has a fused thiophene ring system that is two rings larger than that of the starting material thiophene moiety 26. Alternatively, the α,α'-dihydro-β,β'-dibromo thiophene moiety 26 can be subjected to a first series of R-acylation/reaction with 2-mercaptoacetate/cyclization/decarboxylation reactions, then to a second series of reactions with a different R' group in the acylation step to provide a β''-(R-substituted)-β'''-(R'-substituted) fused thiophene moiety in which R and R' are different from one another.

Figure 5:
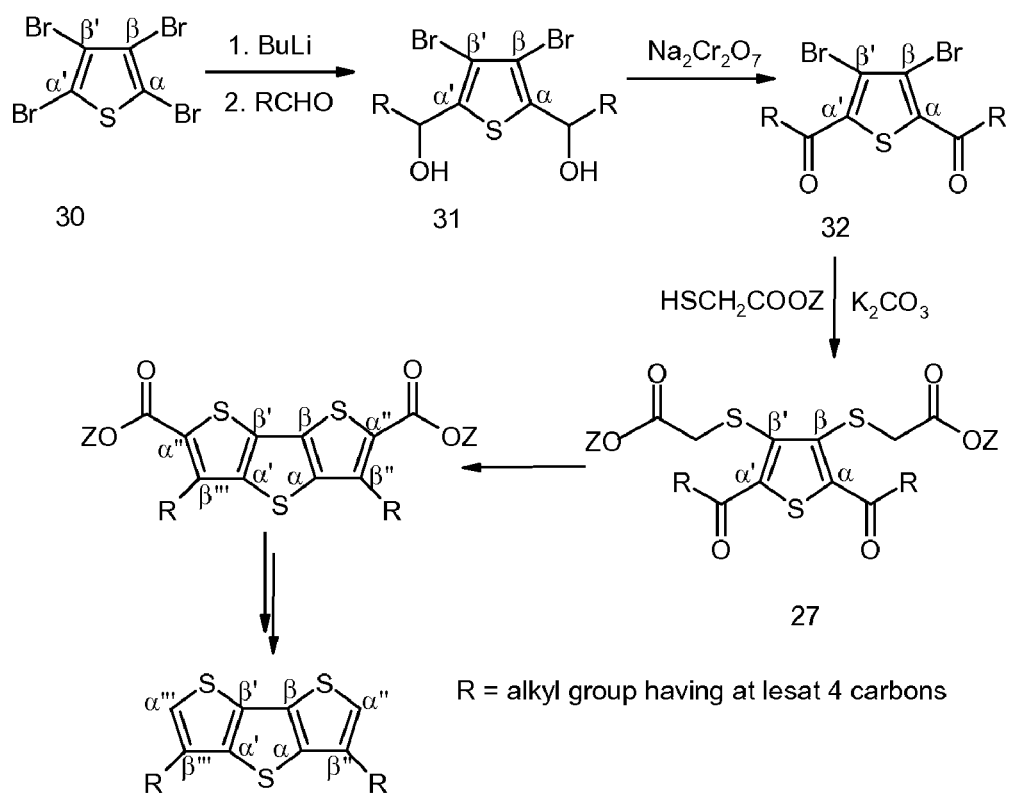
FIG. 5 is a reaction scheme showing an alternative method for making an α,α'-bis(R-acyl)-β,β'-bis(carboxymethylthio) thiophene moiety.

The reaction scheme of FIG. 5 shows an alternative way to make an α,α'-bis(R-acyl)-β,β'-bis(carboxymethylthio) thiophene moiety 27. An α,α',β,β'-tetrabromo thiophene moiety 30 is lithiated (selectively at the α-positions) and reacted with an aldehyde RCHO to form diol 31, which is oxidized to form α,α'-bis(R-acyl)-β,β'-dibromo thiophene moiety 32, which is reacted with a 2-mercaptoacetate to form the α,α'-bis(R-acyl)-β,β'-bis(carboxymethylthio) thiophene moiety 27.

Figure 6:
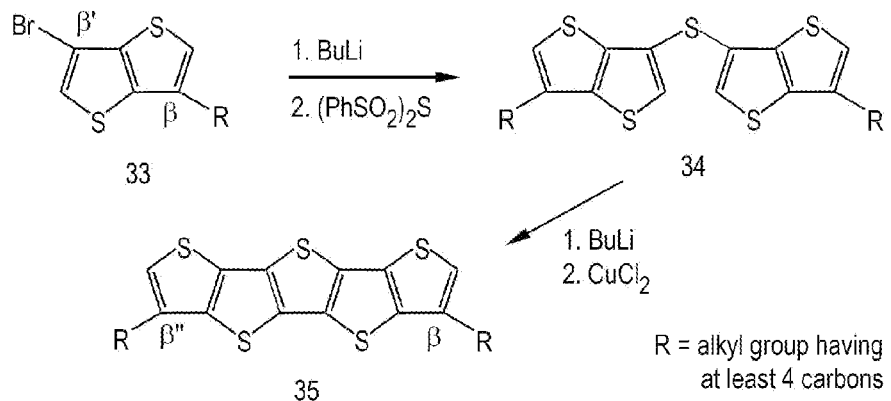
FIG. 6 is a reaction scheme showing a method for making a five-ring fused thiophene.

Fused thiophene moieties having relatively large fused thiophene ring systems can be synthesized using the reaction schemes described above. It is also possible to build large fused thiophene ring systems using the coupling and ring closure steps shown in the reaction scheme of FIG. 6. A β-R-substituted-β'-bromo thiophene moiety 33, in which R is an alkyl group, is used as the starting material in this scheme; synthetic routes to 33 are described below. While in the reaction scheme of FIG. 6, the β-R-substituted-β'-bromo thiophene moiety 33 is shown as having a thieno[3,2-b] thiophene ring system, it may also have a monocyclic thiophene, or a larger fused thiophene ring system as described above at its core. The β-R-substituted-β'-bromo thiophene moiety 33 is lithiated and reacted with sulfur bis (phenylsulfonate) (or sulfur dichloride) to form coupled thioether 34, which is lithiated and subjected to oxidative ring closure using $CuCl_2$ to form the β,β'' disubstituted fused thiophene moiety 35.

Figure 7:
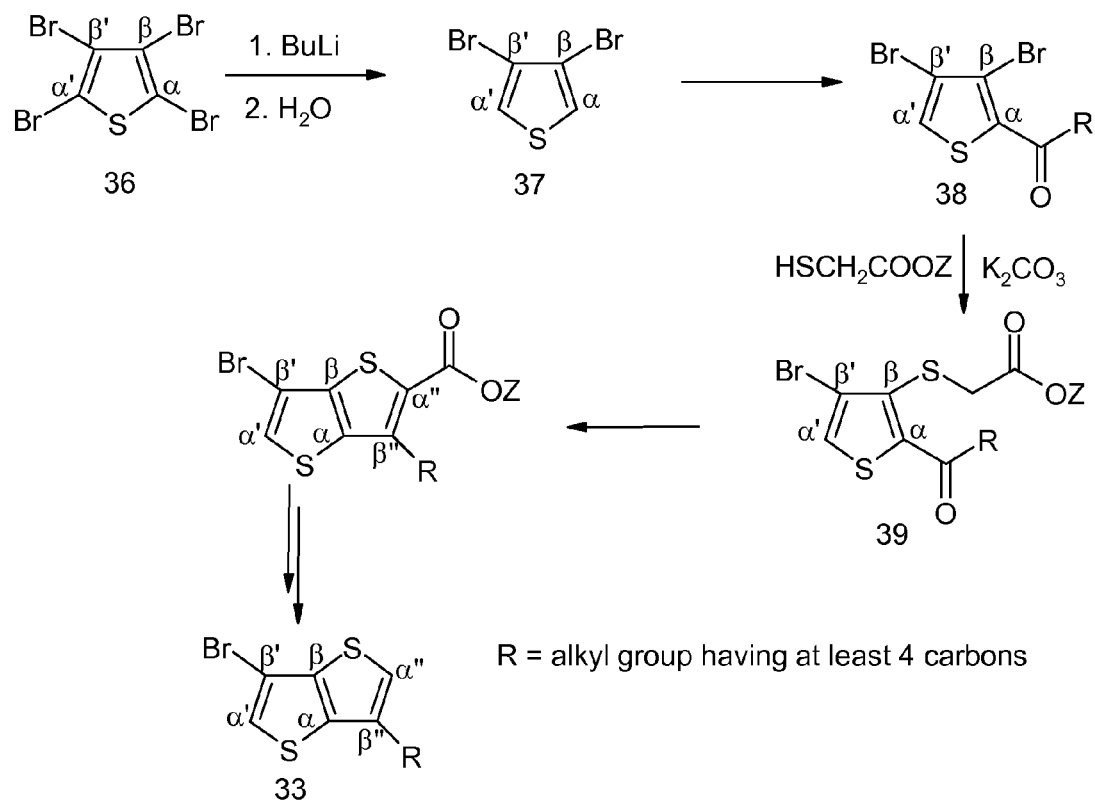
FIG. 7 is a reaction scheme showing a method for making polycyclic β-R-substituted-β'-bromo thiophene moieties.

Polycyclic β-R-substituted-β'-bromo thiophene moieties can be made by performing the reaction series of FIG. 2 on a β'-bromo thiophene moiety, as shown in the reaction scheme of FIG. 7. Tetrabromothiophene is dilithiated (selectively at the α-positions) and protonated to yield dibromothiophene 37, which is acylated (giving 38) and reacted with a 2-mercaptoacetate to give α-(R-acyl)-β-carboxymethylthio-β'-bromo thiophene moiety 39, which is cyclized and decarboxylated to yield 33. While the starting material in the reaction scheme of FIG. 7 is a monocyclic thiophene, polycyclic fused thiophene starting materials can be used as well.

In another aspect, described herein are β-R-substituted-β'-bromo thiophene compounds, in which R is an alkyl group as defined herein. For example, compounds described herein include those having structure 40, below. R can be, for example, an unsubstituted alkyl group.

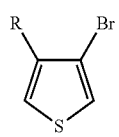

40

The unsubstituted alkyl group according to this aspect can be a straight-chain alkyl group (e.g. butyl, pentyl, hexyl, heptyl, octyl, nonyl, decyl, undecyl, dodecyl or hexadecyl), a branched alkyl group (e.g. sec-butyl, neo-pentyl, 4-methylpentyl), or a substituted or unsubstituted cycloalkyl group (e.g. cyclopentyl, cyclohexyl). In one aspect, R can be an alkyl group, itself at least seven, at least eight, at least nine, or at least ten carbons in size, which is substituted or unsubstituted. In one aspect, the substitution of the alkyl group is separated from the fused thiophene ring system by at least two carbons. Examples of substituted alkyl groups according to this aspect include 6-hydroxyhexyl and 3-phenylbutyl. The selection of $R_1$ and $R_2$ moieties depends upon the end use of the fused thiophene moiety-containing composition. Any functionality on the substituted alkyl group can be protected in order to survive subsequent reaction steps. Unsubstituted thiophene-based compositions tend to be relatively insoluble; as such, in one aspect, R can be an alkyl group having at least six carbons in size. For example, alkyl groups for improving solubility include $C_kH_{2k-1}$, where k is an integer greater than or equal to six.

Figure 8:
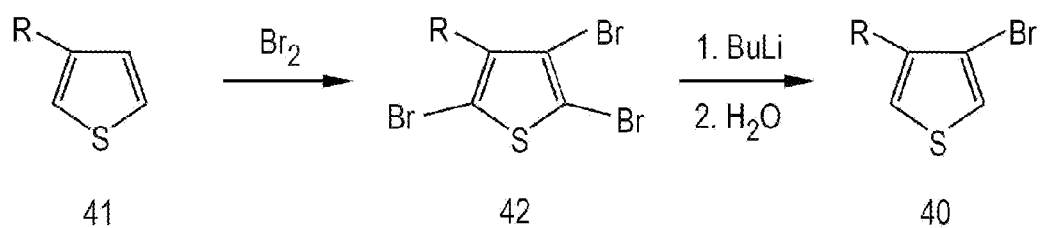
FIG. 8 is a reaction scheme showing a method for making β-R-substituted-β'-bromo thiophene compounds.
Figure 9:
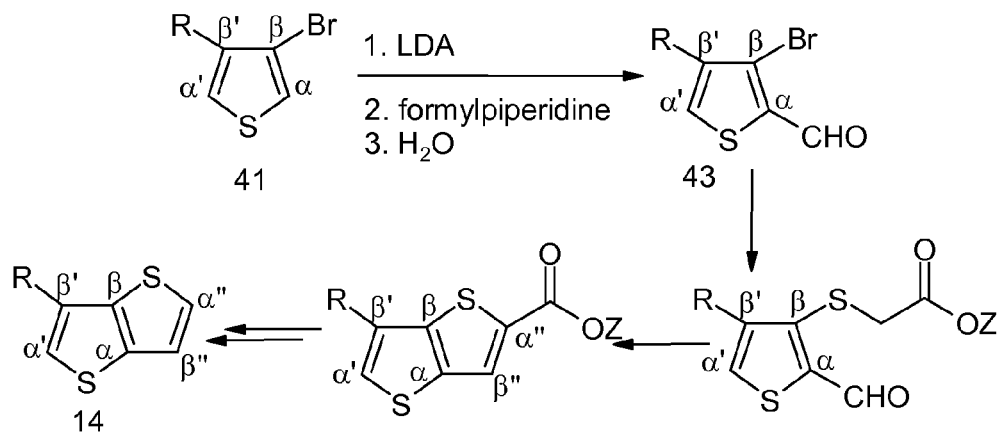
FIG. 9 is reaction scheme showing a method for making monosubstituted fused thiophene moieties.

In one aspect, compounds having structure 40 above can be synthesized from β-R-substituted thiophene moieties by the bromination/debromination method shown in FIG. 8. β-R-substituted thiophene 41 is fully brominated with molecular bromine to yield the tribrominated compound 42, which is selectively lithiated and protonated at the α-positions to yield the desired β-R-substituted-β'-bromo thiophene 40. The method of FIG. 8 can also be used to make β-brominated fused thiophene moieties from fused thiophene moieties. The monocyclic β-R-substituted-β'-bromo thiophene 40 can be used to make tricyclic bis(R-substituted) fused thiophene moieties according to the reaction scheme shown in FIG. 6. The monocyclic β-R-substituted-β'-bromo thiophene 40 can also be used to make monosubstituted fused thiophene moieties according to the reaction scheme shown in FIG. 9. For example, monocyclic thiophene 40 is lithiated and reacted with formylpiperidine, and the adduct is hydrolyzed to yield aldehyde 43, which is reacted with a 2-mercaptoacetate, cyclized and decarboxylated to yield β-R-substituted fused thiophene 14.

In one aspect, any of the sulfur atoms present in the fused thiophene compounds described herein can be oxidized to produce $SO_2$. In another aspect, a composition includes at least one of the following oxidized fused thiophene moieties:

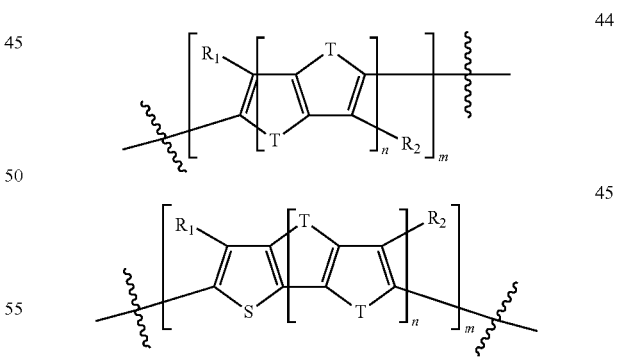

In one aspect, with respect to structures 44 and 45, n is an integer greater than zero; m is no less than one; $R_1$ and $R_2$ are, independently, hydrogen or an alkyl group, wherein each T is, independently, S or $SO_2$, wherein T is $SO_2$ in at least one of the central-most rings of the oxidized fused thiophene ring system, and wherein when the fused thiophene moiety has the formula 45, n is not 1. Each T is independently S and $SO_2$, where T is $SO_2$ in at least one of the central-most rings of the fused thiophene ring system. As used herein, the central-most ring of a fused thiophene ring system having an odd number $2q+1$ of fused rings is the $q+1^{th}$ ring from an end of the ring system. The central-most rings of a fused thiophene ring system having an even number $2q$ of fused rings are the $q^{th}$ and $q+1^{th}$ rings from an end of the ring system. For example, the central-most ring of a three-ring system is the second ring, the central-most rings of a four-ring system are the second and third rings, and the central-most ring of a five-ring system is the third ring.

Any of the oxidized fused thiophene compounds described herein can be used in polymers, oligomers, monomers, chromophores, and other compositions as described above. For example, the at least one oxidized fused thiophene moiety can be present in the composition at a total concentration of at least 1 wt %. The value of n can be, for example, 1, 2, 3, 4, or 5. In other aspects, the fused thiophene moiety is tricyclic or greater (i.e., 45, $n \leq 1$; or 44, $n \leq 2$). In further aspects, at least one of $R_1$ and $R_2$ is an alkyl group at least six carbons in size directly bound to the oxidized fused thiophene ring system core of the oxidized fused thiophene moiety. Both $R_1$ and $R_2$ can be alkyl groups, and can be the same as or different from one another. In certain aspects, neither $R_1$ nor $R_2$ is H. In other aspects, the composition has a ratio of β-hydrogen to oxidized fused thiophene ring systems of less than about 1/10, 1/9, 1/8, 1/7, or 1/6. In one aspect, the oxidized fused compounds have the structure

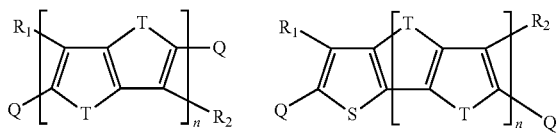

wherein n is an integer greater than zero; $R_1$ and $R_2$ are, independently, hydrogen or an alkyl group, and Q is, independently, hydrogen, an alkyl group, an acyl halide, an ester, an aldehyde, a ketone, a hydroxyl group, a thiol group or alkyl substituted thiol group, an alkoxy group, an acrylate group, an amino group, a vinyl ether, or a halide.

The oxidized fused thiophene compounds described herein can be incorporated in a conjugated fused thiophene polymers or oligomers having m>1. Alternatively, the oxidized fused thiophene compound can be incorporated in a polymer comprising a polyester, a polyurethane, a polyamide, a polyketone, a polyacrylate, a polymethacrylate, or a poly(vinyl ether).

The oxidized fused thiophene compounds and moieties described herein can be prepared by oxidation, for example, with MCPBA. Oxidation is generally selective at the central-most rings of the polycyclic fused thiophene ring systems; however, it is contemplated that any of the sulfur atoms in the fused thiophenes can be oxidized. Examples of oxidized fused thiophene moieties are shown below as structures 46, 47, 48 and 49

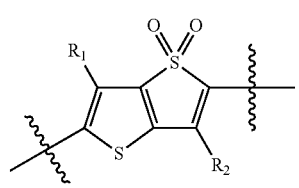

46

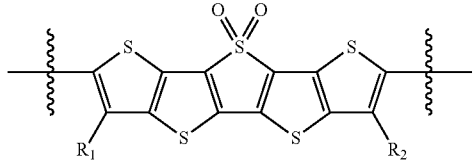

47

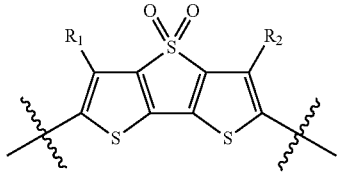

48

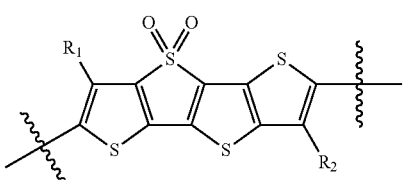

49

Fused thiophene and oxidized fused thiophene oligomers and polymers can be prepared using methodologies similar to those used in making oligo- and poly(thiophenes) described above. For example, α,α'-dihydro fused thiophene moieties can be oxidatively oligomerized or polymerized using iron (III) compounds (e.g., $FeCl_3$, $Fe(acac)_3$), or can be brominated and coupled in an organomagnesium mediated reaction. The fused thiophene moieties and oxidized fused thiophene moieties described herein can be incorporated into other conjugated polymers such as, for example phenylene, vinylene, and acetylene copolymers, using coupling reactions familiar to the skilled artisan. The fused thiophene moieties and oxidized fused thiophene moieties described herein can be incorporated into other main chain and side chain polymers using techniques known in the art. It is contemplated that the fused thiophene compound can be oxidized prior to incorporation into an oligomer or polymer. In the alternative, the fused thiophene compound can be incorporated into the oligomer or polymer followed by oxidation.

EXAMPLES

The following examples are put forth so as to provide those of ordinary skill in the art with a complete disclosure and description of how the materials, articles, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Figure 10:
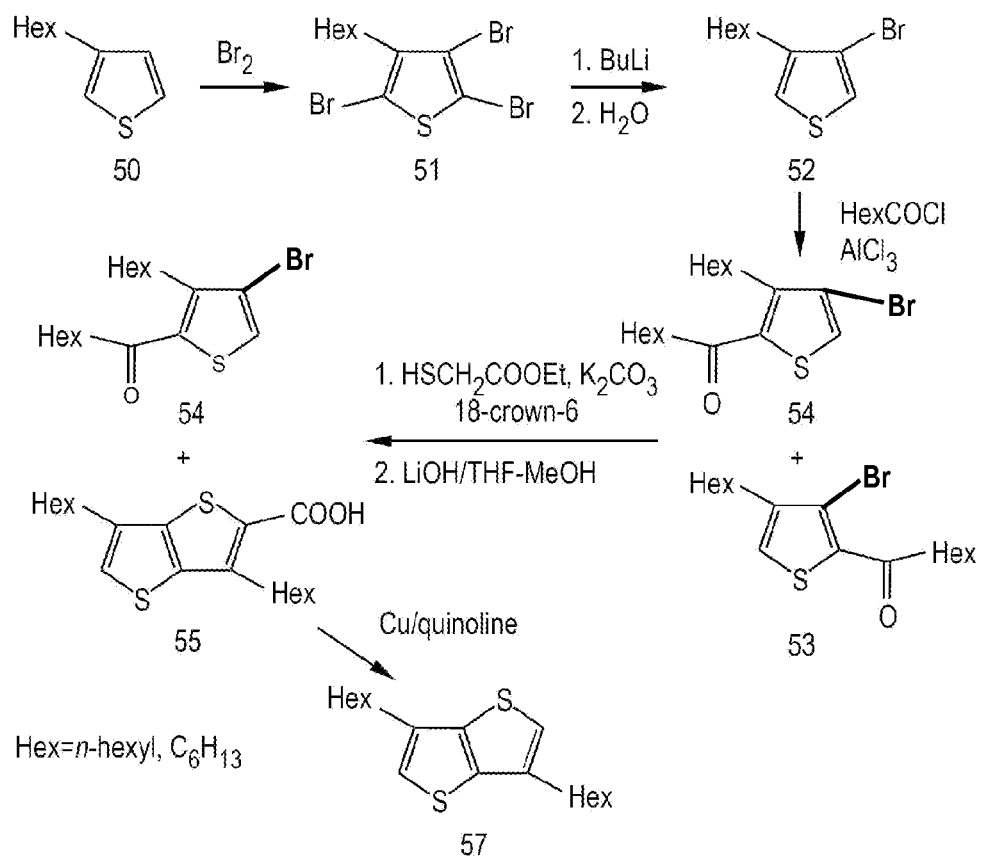
FIG. 10 is a reaction scheme showing the synthesis of 3,6-dihexylthieno[3,2-b]thiophene and 3,6-didecylthieno[3,2-b]thiophene according to Example 1.

Example 1 di-β-substituted thieno[3,2-b]thiophenes 3,6-dihexylthieno[3,2-b]thiophene 57 was synthesized as shown in the reaction scheme of FIG. 10.

2,4,5-Tribromo-3-hexylthiophene (51). 3-Hexylthiophene (50) (100 g, 0.595 mol) was mixed with 200 mL acetic acid. To this mixture, bromine (88 mL, 1.33 mol) was added dropwise. After addition of the bromine, the resulting mixture was stirred at room temperature for 4 hours, heated at 60-70° C. overnight, then poured into 800 mL ice water and neutralized with 6M aqueous NaOH. The mixture was extracted with ethyl acetate (3×100 mL). The combined organic layers were washed with brine (2×100 mL) and water (100 mL) and dried over $MgSO_4$. Evaporation of the solvent yielded crude 51 (234 g, 97.1% crude yield). This crude product was sufficiently pure for use in subsequent reactions. GC/MS: 404 g/mol (M−1). $^1$H NMR ($CD_2Cl_2$): δ 2.64 (t, 2H), 1.51 (m, 2H), 1.32 (m, 6H), 0.89 (t, 3H). $^{13}$C NMR: 143.69, 117.86, 111.48, 110.18, 33.62, 32.86, 30.96, 30.52, 24.70, 16.00.

3-Bromo-4-hexylthiophene (52). Compound 51 (70 g, 0.173 mol) was mixed with dry THF (400 mL). To this mixture, n-butyllithium (138 mL, 2.5M in hexane, 0.345 mol) was added dropwise at −78° C. under argon. The resulting mixture was stirred for 10 minutes, then water (30 mL) was added to quench the reaction. The THF was evaporated and the organic was extracted with ethyl acetate (2×100 mL). The combined organic layers were washed with brine (2×100 mL), water (70 mL) and dried over $MgSO_4$. After evaporation of the solvent, the resulting crude product was purified by vacuum distillation (72-74° C. at 0.17 mbar) to yield 52 (35.3 g, 82.6% yield). GC/MS: 246 g/mol (M−1). $^1$H NMR ($CD_2Cl_2$): δ 7.22 (s, 1H), 6.96 (s, 1H), 2.57 (t, 2H), 1.61 (m, 2H), 1.32 (m, 6H), 0.88 (t, 3H). $^{13}$C NMR: 141.92, 122.87, 120.95, 112.89, 31.88, 30.07, 29.53, 29.20, 22.88, 14.14.

1-(3-Bromo-4-hexyl-2-thienyl)heptanone (53). To a mixture of compound 52 (24.7 g, 0.1 mol) and $AlCl_3$ (26.8 g, 0.2 mol) in dry $CH_2Cl_2$ (100 mL), heptanoyl chloride (14.9 g, 0.1 mol) was added dropwise at room temperature. This mixture was stirred for two hours, after which time GC/MS analysis indicated that a 3:1 mixture of target compound 53 and its regioisomer 1-(4-bromo-3-hexyl-2-thienyl)heptanone (54) had been formed. The reaction mixture was poured into 200 mL 6 M HCl and washed with water (3×50 mL). The organic layer was then dried over $MgSO_4$; evaporation of the solvent yielded 34.7 g of a crude mixture of compounds 53 and 54, which was used without separation or further purification in the next reaction.

3,6-Dihexylthieno[3,2-b]thiophene-2-carboxylic acid (55). The mixture of compounds 53 and 54 (66.5 grams, 0.185 mol) was mixed with $K_2CO_3$ (53.6 grams, 0.39 mol) and a catalytic amount of 18-crown-6 in 200 mL DMF. To this mixture, ethyl 2-mercaptoacetate (20.3 mL, 0.185 mol) was added dropwise at 60-70° C. The reaction mixture was stirred at 60-70° C. overnight, then poured into water (800 mL). The organic component was extracted with ethyl acetate (3×100 mL) and the combined organic extracts were washed with brine (2×100 mL) and water (100 mL). The solvent was removed by evaporation, and the residue was dissolved in THF (300 mL), forming a solution to which LiOH (84 mL, 10% solution in water), MeOH (50 mL) and a catalytic amount of tetrabutylammonium iodide were added. The mixture was heated at reflux for 3 hours, after which time the solvent was removed by evaporation, and the residue acidified with concentrated HCl (50 mL). After dilution with 200 mL water, the organic component was extracted with ethyl acetate (3×100 mL). The combined organic layers were washed with brine (2×100 mL), water (100 mL) and dried over $MgSO_4$. After evaporation of the solvent, the compound 55 was separated from unreacted compound 54 using column chromatography ($SiO_2$/5% ethyl acetate in hexane with 20% ethyl acetate in hexane to fully elute the compound 55), providing pure compound 55 (30 g, 46.1% yield). $^1$H NMR ($CD_2Cl_2$): δ 7.24 (s, 1H), 3.18 (t, 2H), 2.73 (t, 2H), 1.75 (m, 4H), 1.34 (m, 14H), 0.89 (m, 6H). $^{13}$C NMR: 169.15, 146.25, 143.10, 141.49, 136.14, 126.67, 126.11, 31.99, 29.74 (6C), 22.99, 14.24.

3,6-Dihexylthieno[3,2-b]thiophene (57). A mixture of compound 55 (30 g, 0.085 mol), copper powder (3.76 g) and quinoline (80 mL) was heated at 264-260° C. in a Woods metal bath. When no further bubbles of carbon dioxide gas could be detected (about 2 hours), the mixture was allowed to cool to room temperature and hexane (200 mL) was added. This mixture was washed repeatedly with HCl (1-2 M in water) to remove the quinoline. The remaining organic layer was dried over $MgSO_4$ and concentrated by evaporation, leaving a residue, which was purified by column chromatography ($SiO_2$/hexanes) to yield compound 57 (18 g, 68.4%). m.p. 57.5-59.1° C., $^1$H NMR ($CD_2Cl_2$): δ 6.97 (s, 2H), 2.70 (t, 4H), 1.73 (m, 4H), 1.37 (m, 12H), 0.88 (t, 6H). $^{13}$C NMR: 136.56, 134.96, 109.80, 31.94, 29.31, 29.28, 28.47, 22.96, 14.22.

The same reaction sequence was used to make 3,6-didecylthieno[3,2-b]thiophene (58).

Example 2 mono-β-substituted thieno[3,2-b]thiophenes

Figure 11:
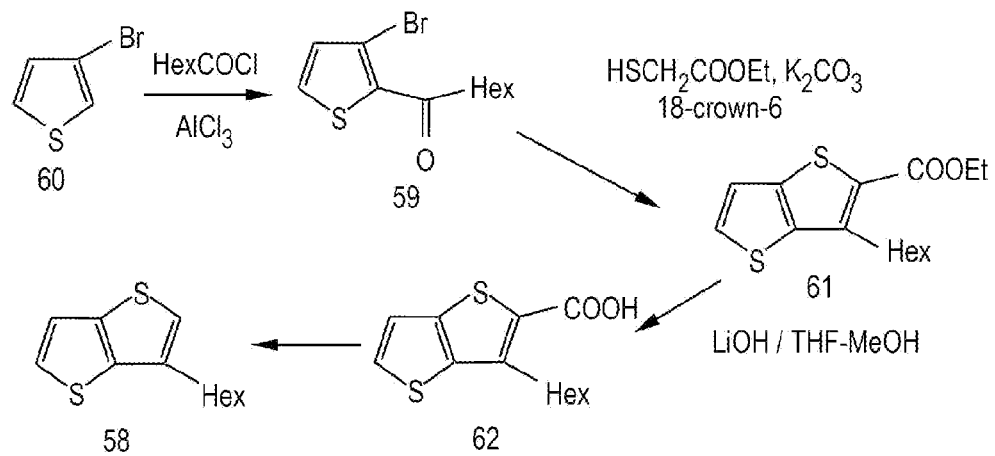
FIG. 11 is a reaction scheme showing the synthesis of 3-hexylthieno[3,2-b]thiophene according to Example 2.

3-Hexylthieno[3,2-b]thiophene 58 was synthesized as shown in the reaction scheme of FIG. 11.

1-(3-Bromothienyl)heptanone (59). To a mixture of 3-bromothiophene (60) (16.3 g, 0.1 mol), $AlCl_3$ (26.8 g, 0.2 mol) and $CH_2Cl_2$ (100 mL), heptanoyl chloride (14.9 g, 0.1 mol) was added dropwise at room temperature. The resulting mixture was stirred for two hours after which time GC/MS indicated complete conversion of compound 60 to compound 59. The reaction mixture was poured into cold HCl (6M, 200 mL). The organic component was extracted with hexane (3×100 mL). The combined organic layers were washed with brine (2×100 mL) and water (100 mL). After drying over $MgSO_4$, the crude target compound was purified by column chromatography ($SiO_2$/hexanes) to yield compound 59 (25.1 g, 91.3% yield). GC/MS: 275 g/mol (M) $^1$H NMR ($CD_2Cl_2$) δ 7.53 (d, 1H), 7.12 (d, 1H), 3.01 (t, 2H), 1.71 (m, 2H), 1.38 (m, 6H), 0.92 (t, 3H).

Ethyl 3-hexylthieno[3,2-b]thiophene-2-carboxylate (61). Compound 59 (35.4 g, 0.13 mol) and $K_2CO_3$ (27.6 g, 0.2 mol) were mixed with N,N-dimethylformamide (100 mL). A catalytic amount (~25 mg) 18-crown-6 was added, and to this mixture, ethyl 2-mercaptoacetate (14.0 mL, 0.13 mol) was added dropwise at 60° C. The mixture was stirred overnight and poured into water (500 mL). The organic component was extracted with ethyl acetate (3×80 mL). The combined organic layers were washed with brine (2×100 mL) and water (100 mL). Organic layer was then dried over $MgSO_4$. After evaporation of the solvent, the crude compound 61 was obtained and purified by column chromatography ($SiO_2$/5% ethyl acetate in hexanes) to yield pure compound 61 (32.1 g, 84.5%). GC/MS: 296 g/mol (M). $^1$H NMR ($CD_2Cl_2$) δ 7.56 (d, 1H), 7.24 (d, 1H), 4.34 (q, 2H), 3.15 (t, 2H), 1.71 (m, 2H), 1.32 (m, 6H), 0.88 (m, 6H). $^{13}$C NMR: 163.24, 143.31, 141.85, 141.09, 131.13, 128.44, 120.35, 61.25, 31.99, 29.72 (overlap), 22.98, 14.52, 14.23.

3-Hexylthieno[3,2-b]thiophene-2-carboxylic acid (62). Compound 61 (32.1 g, 0.11 mol) was mixed with LiOH (10% in water, 50 mL), THF (100 mL), MeOH (30 mL) and a catalytic amount (~20 mg) tetrabutylammonium iodide in a 500 mL flask. This mixture was heated at reflux overnight, allowed to cool to room temperature, and acidified with concentrated HCl. The resultant yellow solid was collected by filtration and washed thoroughly with water. The solid then was heated with hexane (100 mL) allowed to cool to room temperature. After filtration, the solid was collected, dried over vacuum to yield compound 62 as a light yellow powder (28.0 g, 96.7%). Mp: 110.7-112.4° C.

3-Hexylthieno[3,2-b]thiophene (58). A mixture of compound 62 (14.6 g, 0.054 mol), copper powder (2.00 g), and quinoline (80 mL) was heated at about 260° C. in a Woods metal bath. When no further bubbles of $CO_2$ were detected (about 2 hours), the mixture was allowed to cool to room temperature, and hexane (200 mL) was added. The mixture was washed repeatedly with HCL (1-2 M in water) to remove the quinoline. The organic layer was dried over $MgSO_4$ and concentrated by evaporation. The residue was purified by column chromatography ($SiO_2$/hexanes) to yield compound 58 (25.1 g, 90.3%). GC/MS: 224 g/mol (M). $^1$H NMR ($CD_2Cl_2$) δ 7.36 (m, 1H), 7.25 (m, 1H), 7.01 (m, 1H), 2.73 (t, 2H), 1.69 (m, 4H), 1.34 (m, 6H), 0.89 (t, 3H). $^{13}$C NMR: 140.39, 139.13, 135.39, 127.01, 122.19, 120.26, 32.01, 30.29, 29.43, 23.01, 14.24.

Example 3 di-β-substituted dithieno[3,2-b:2'-3'-d]thiophenes and di-β-substituted dithieno[3,2-b:2'-3'-d]thiophene-4,4-dioxides.

Figure 12:
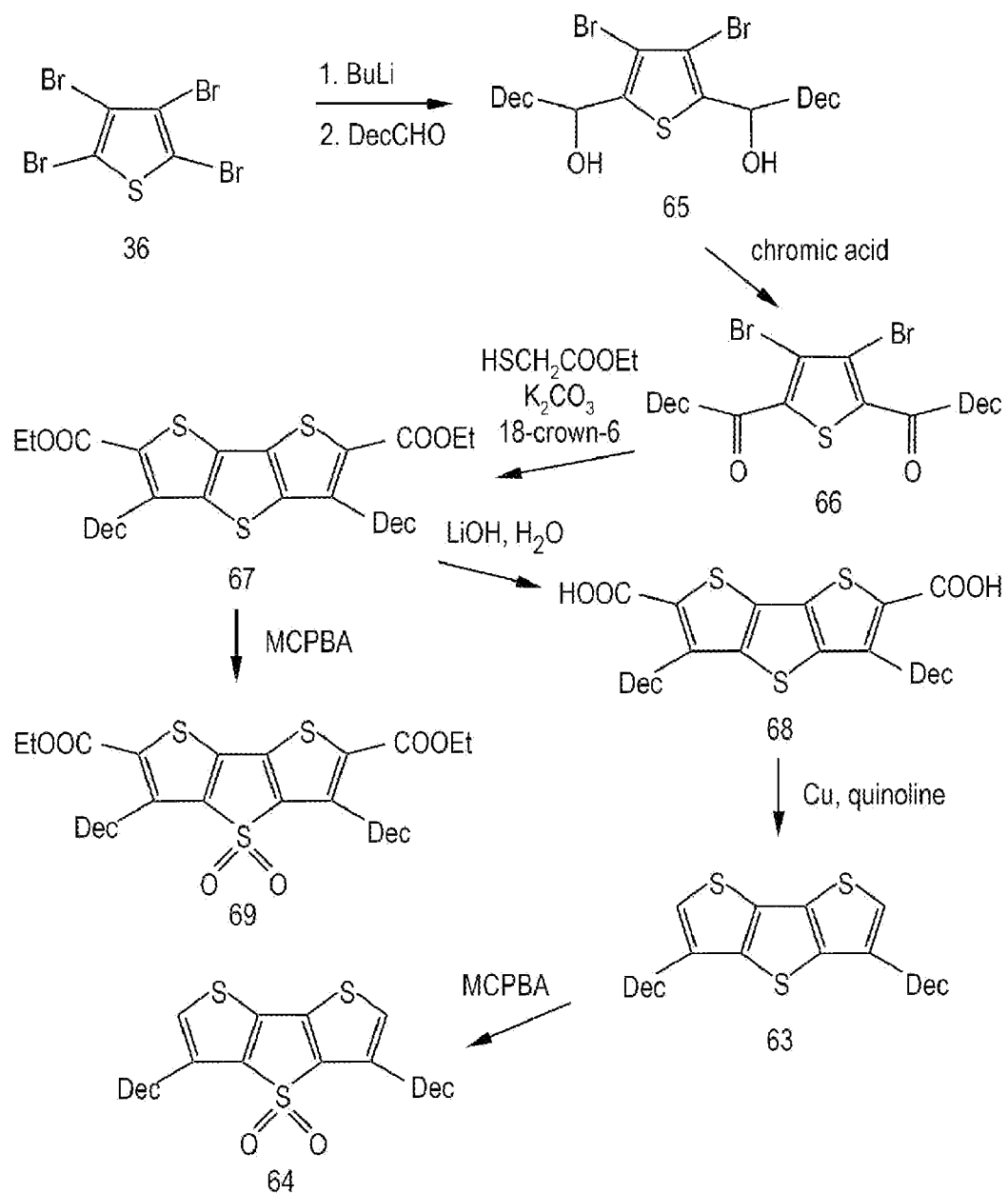
FIG. 12 is a reaction scheme showing the synthesis of 3,6-didecylthieno[3,2-b]thiophene and 3,6-didecylthieno[3,2-b]thiophene-4,4-dioxide according to Example 3.

3,6-didecylthieno[3,2-b]thiophene 63 and 3,6-didecylthieno[3,2-b]thiophene-4,4-dioxide 64 were synthesized as shown in the reaction scheme of FIG. 12.

1,1'-(3,4-Bromo-2,5-thienyl)diundecanol (65). To a solution of tetrabromothiophene 36 (80.0 g, 0.2 mol) and THF (500 mL), butyllithium (160 mL, 0.4 mol, 2.5M in hexanes) was added dropwise at −78° C. Undecylic aldehyde (Dec-CHO) (69.7 g, 0.41 mol) was added, and the reaction mixture was stirred for two hours. The THF solvent was then removed by evaporation, and the organic residue was extracted with hexanes. The combined organic layers were washed by brine (2×100 mL) and water (100 mL) and dried over $MgSO_4$. The crude product was purified by column chromatography ($SiO_2$/5% ethyl acetate in hexanes) to yield compound 65 (84.1 grams, 72.5% yield). $^1$H NMR ($CD_2Cl_2$) δ 5.02 (broad, 2H), 1.79 (m 4H), 1.28 (m, 32H), 0.88 (t, 6H). $^{13}$C NMR: 143.25, 109.67, 70.53, 38.31, 31.96, 29.75, 29.70, 29.61, 29.55, 29.21, 25.68, 22.84, 14.09.

1,1'-(3,4-bromo-2,5-thienyl)diundecanone (66). A chromic acid solution was prepared by dissolving 100 grams of sodium dichromate dihydrate (0.34 mol) was dissolved into water (300 mL), then 136 grams of concentrated sulfuric acid was added, and the resulting solution was diluted to 500 mL. Compound 65 (80.0 g, 0.137 mol) was mixed with acetone (300 mL). To this mixture, chromic acid solution (260 mL) was added dropwise at room temperature. The mixture was stirred overnight, after which time considerable solid had formed in the reaction mixture. Most of the acetone was decanted and the rest of mixture was extracted with ethyl acetate (2×100 mL). The combined organic layers were washed with brine (3×50 mL) and dried over $MgSO_4$. The solvent was evaporated, and the residue was mixed with ethanol (100 mL) and white and pure compound 66 solidified and was collected by filtration (72.0 g, 90.5% yield). M.p. 69.5-70.8° C. $^1$H NMR ($CD_2Cl_2$) δ 3.07 (t, 4H), 1.74 (m, 4H), 1.28 (m, 28H), 0.88 (t, 6H). $^{13}$C NMR: 192.49, 141.99, 118.82, 42.03, 32.13, 29.79, 29.71, 29.62, 29.55, 29.29, 24.16, 22.92, 14.11.

Diethyl 3,5-didecyldithieno[3,2-b:2',3'-d]thiophene-2,6-dicarboxylate (67). Compound 66 (30.0 g, 0.052 mol) was mixed with $K_2CO_3$ (28.7 g, 0.21 mol) and N,N-dimethylformamide (100 mL). To this mixture, ethyl 2-mercaptoacetate (11.5 mL, 0.104 mol) was added dropwise at 60° C. The reaction mixture was stirred for 48 hours at 60° C. under nitrogen, then was poured into water (500 mL). The organic component was extracted with ethyl acetate (3×100 mL). The combined organic layers were washed with brine (2×100 mL) and water (50 mL) and dried over $MgSO_4$. The solvent was evaporated, and the residue was purified by column chromatography ($SiO_2$/5% ethyl acetate in hexanes) to give compound 67 as sticky, low melting point solid (19.1 g, 59.3% yield). $^1$H NMR ($CD_2Cl_2$) δ 4.36 (q. 4H), 3.15 (t, 4H), 1.73 (m, 4H), 1.39 (m, 36H), 0.87 (m, 6H). $^{13}$C NMR: 162.86, 145.47, 144.51, 133.05, 128.99, 61.63, 32.33, 29.99 (overlap), 23.11, 14.53, 14.31.

3,5-Didecanyldithieno[3,2-b:2',3'-d]thiophene-2,6-dicarboxylic acid (68). Compound 66 (10.2 g, 0.017 mol) was mixed with LiOH (1.0 g in 10 mL water), THF (100 mL), MeOH (20 mL) and a catalytic amount (~35 mg) of tetrabutylammonium iodide. This mixture was heated at reflux overnight, then most of the solvent was evaporated. The residue was acidified with concentrated HCl (30 mL), forming a solid which was collected by filtration, washed thoroughly with water, and vacuum dried to yield compound 68 (8.6 g, 98% yield). M.p. 280.1° C. $^1$H NMR ($CD_2Cl_2$) δ 3.24 (t, 4H), 1.72 (m, 2H), 1.29 (m, 30H), 0.88 (t, 6H). $^{13}$C NMR: 168.46, 148.24, 146.58, 136.32, 35.91, 33.64, 28.91 (m, overlap), 26.60, 17.49.

3,5-Didecyldithieno[3,2-b:2',3'-d]thiophene (63). Compound 68 (8.6 g, 0.016 mol), copper powder (0.7 g) and quinoline (50 mL) were combined and heated at 250-260° C. in a Woods-metal bath. When no further bubbles of carbon dioxide gas could be detected (about 2 hours), the mixture was cooled to room temperature and hexane (200 mL) was added. This mixture was washed repeatedly with HCl (1-2 M in water) to remove quinoline. The organic layer was dried over $MgSO_4$ and concentrated by evaporation, and the residue was purified by column chromatography ($SiO_2$/hexanes) to yield compound 63 (3.4 g, 47.4%). $^1$H NMR ($CD_2Cl_2$) δ 6.97 (s, 2H), 2.73 (t, 4H), 1.78 (m, 4H), 1.27 (m, 28H), 0.88 (t, 6H). $^{13}$C NMR: 141.89, 136.75, 130.99, 120.57, 32.33, 30.02, 29.79 (m, overlap), 29.74, 29.15, 23.10, 14.28.

Compounds 64 and 69 were prepared using the method described in Sogiu et al., Rigid-Core Fluorescent Oligothiophene-S,S-dioxide Isothiocyantes. Synthesis, Optical Characterization, and Conjugation to Monoclonal Antibodies, J. Org. Chem. 2003, 68, 1512-1520, which is incorporated herein by reference.

3,5-Didecyldithieno[3,2-b:2',3'-d]thiophene-4,4-dioxide (64). 3-chloroperbenzoic acid (6.1 g, 0.035 mol), in 20 mL $CH_2Cl_2$ was added dropwise to a solution of 63 (3.64 g, 8.18 mmol) in 20 mL dichloromethane. The mixture was stirred at room temperature overnight, then washing sequentially with 10% KOH, 10% $NaHCO_3$ and brine. The organic layer was dried over $Mg_2SO_4$, and the solvent was removed by evaporation. The crude product was purified by column chromatography ($SiO_2$/5% ethyl acetate in hexanes) to give compound 64 as a yellow solid (1.4 g, 35.9% yield). M.p. 58.7-

60.3° C. $^1$H NMR (CD$_2$Cl$_2$) δ 6.94 (s, 2H), 2.73 (t, 4H), 1.72 (m, 4H), 1.27 (m, 28H), 0.88 (t, 6H). $^{13}$C NMR: 142.99, 139.06, 136.36, 124.51, 32.27, 30.11, 29.95, 29.91, 29.68, 29.48, 29.51, 28.51, 23.04, 14.22.

Diethyl 3,5-didecyldithieno[3,2-b:2',3'-d]thiophene-4,4-dioxide-2,6-dicarboxylate (69). 3-chloroperbenzoic acid (1.2 g, 6.9 mmol), in 20 mL CH$_2$Cl$_2$ was added dropwise to a solution of 67 (3.64 g, 8.18 mmol) in 20 mL dichloromethane. The mixture was stirred at room temperature overnight, then washing sequentially with 10% KOH, 10% NaHCO$_3$ and brine. The organic layer was dried over MgSO$_4$, and the solvent was removed by evaporation. The crude product was purified by column chromatography (SiO$_2$/5% ethyl acetate in hexanes) to give compound 69 as a waxy solid (0.56 g, 53% yield). $^1$H NMR (CD$_2$Cl$_2$) δ 4.39 (q, 4H), 3.13 (t, 4H), 1.72 (m, 4H), 1.27 (m, 34H), 0.88 (t, 6H). $^{13}$C NMR: 161.41, 145.52, 144.77, 137.56, 132.89, 62.03, 32.11, 30.59, 29.82, 29.78, 29.75, 29.53, 29.49, 27.88, 22.89, 14.21, 14.07.

The reaction scheme of FIG. 12 was also used to make 3,5-dihexyldithieno[3,2-b:2',3'-d]thiophene and 3,5-dihexyldithieno[3,2-b:2',3'-d]thiophene-4,4-dioxide.

Figure 13:
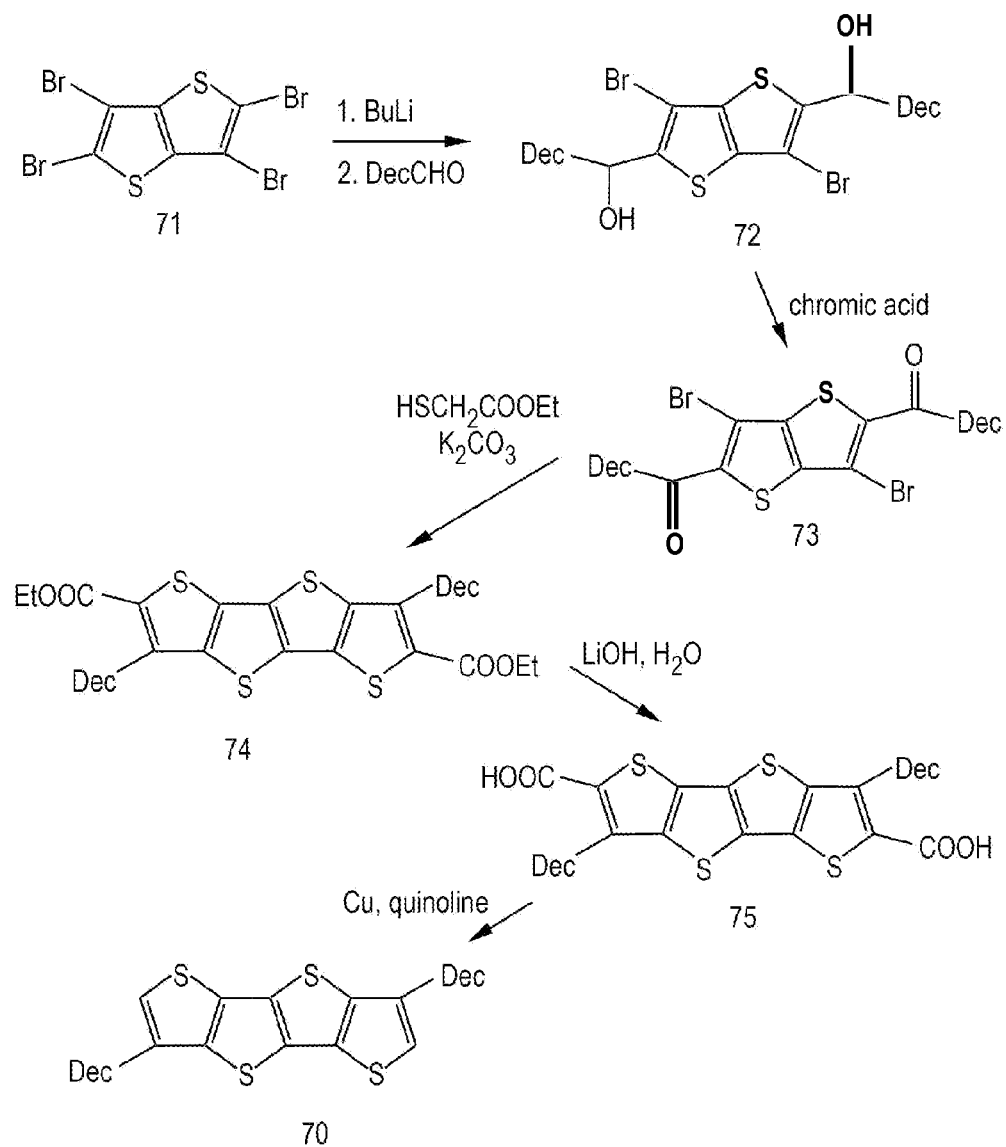
FIG. 13 is a reaction scheme showing the synthesis of 3,7-didecylthieno[3,2-b]thieno[2',3':4,5]thieno[2,3-d]thiophene according to Example 4.

Example 4 di-β-substituted thieno[3,2-b]thieno[2',3':4,5]thieno[2,3-d]thiophenes 3,7-Didecylthieno[3,2-b]thieno[2',3':4,5]thieno[2,3-d]thiophene 70 was synthesized as shown in the reaction scheme of FIG. 13.

2,4-di(1-hydroxydecyl)-3,6-dibromothieno[3,2-b]thiophene (72). 2,3,4,5-tetrabromothieno[3,2-b]thiophene (71) was prepared according to Fuller et al., J. Chem. Soc., Perkin Trans, 1, 1997, 3465, which is hereby incorporated herein by reference. To a mixture of compound 71 (40.0 g, 0.088 mol) in 300 mL dry THF, butyllithium (70 mL, 0.175 mol, 2.5 M in hexanes) was added dropwise at −78° C. The resulting mixture was stirred another 10 to 20 minutes and undecyl aldehyde (30.0 g, 0.176 mol) was added dropwise. The mixture was allowed to warm to room temperature and stirred overnight. Water (20 mL) was added, and the solvent was removed by evaporation. The residue was mixed with hexane (300 mL) and the resultant solid was collected by filtration. This solid then was dried under vacuum, yielding compound 71 that was sufficiently pure for subsequent reaction (47.0 g, 83.9% yield). M.p. 116.0-118.0° C. $^1$H NMR (CD$_2$Cl$_2$) δ 5.15 (m, 2H), 2.31 (broad, 2H), 1.91 (m, 4H), 1.31 (m, 32H), 0.92 (t, 6H). $^{13}$C NMR: 144.06, 109.05, 70.58, 38.77, 32.36, 30.06, 30.04, 29.99, 29.77, 29.65, 26.09, 23.12, 14.29.

2,4-diundecanyl-3,6-dibromothieno[3,2-b]thiophene (73). Compound 72 (30.0 g, 0.047 mol) was mixed with acetone (200 mL). To this mixture, chromic acid solution (130 mL) was added dropwise at room temperature. The mixture was stirred overnight at room temperature, after which time considerable solid had formed in the reaction mixture. Most of the acetone was decanted and the rest of mixture was extracted with ethyl acetate (2×100 mL). The combined organic layers were washed with brine (3×50 mL) and dried over MgSO$_4$. The solvent was evaporated, and the residue was mixed with ethanol (100 mL) and white and pure compound 73 solidified and was collected by filtration (18.4 g, 61.7% yield). M.p. 120.3-121.5° C. $^1$H NMR (CD$_2$Cl$_2$) δ 3.09 (t, 4H), 1.78 (m, 4H), 1.28 (m, 28H), 0.88 (t, 6H). $^{13}$C NMR: 193.15, 143.62, 143.40, 106.70, 41.74, 32.12, 29.79, 29.72, 29.65, 29.55, 29.35, 24.20, 22.91, 14.11.

Diethyl 3,7-didecylthieno[3,2-b]thieno[2',3':4,5]thieno[2,3-d]thiophene 2,6-dicarboxylate (74). Compound 73 was mixed with K$_2$CO$_3$ (16.6 g, 0.12 mol) and N,N-dimethylformamide (100 mL). To this mixture, ethyl 2-mercaptoacetate (6.6 mL, 0.06 mol) was added dropwise at 60° C. The reaction mixture was stirred for 48 hours at 60° C. under nitrogen then was poured into water (500 mL). The resultant solid was collected by filtration. The crude product was then boiled with ethanol (200 mL) and cooled to room temperature. Filtration and drying yielded compound 74 (14.2 g, 72.4% yield). M.p. 130.5-132.2° C. $^1$H NMR (CD$_2$Cl$_2$) δ 4.36 (q, 4H), 3.15 (t, 4H), 1.73 (m, 4H), 1.27 (m, 34H), 0.87 (m, 6H). $^{13}$C NMR: 163.09, 144.79, 144.29, 135.29, 134.28, 128.54, 61.83, 32.57, 30.32, 30.26, 30.21, 30.07, 30.02, 29.98, 29.79, 23.33, 14.79, 14.49.

3,7-Didecylthieno[3,2-b]thieno[2',3':4,5]thieno[2,3-d]thiophene-2,6-dicarboxylc acid (75). Compound 74 (14.0 g, 0.021 mol) was mixed with LiOH (1.24 g, in 15 mL water), THF (100 mL), MeOH (20 mL) and a catalytic amount of tetrabutylammonium iodide. This mixture was heated at reflux overnight and most of the solvent was evaporated. The residue was acidified with concentrated HCl (30 mL). The resultant solid was collected by filtration, washed thoroughly with water and vacuum dried to yield compound 75 (12.5 g, 97.4% yield). M.p. 315.6-318.5° C.

3,7-didecylthieno[3,2-b]thieno[2',3':4,5]thieno[2,3-d]thiophene (70). Compound 75 (13.5 g, 0.021 mol) was mixed with copper powder (0.9 g) in quinoline (80 mL), and the mixture was heated to 250-260° C. in a Woods-metal bath. When no further bubbles of carbon dioxide gas could be detected (about 2 hours), the mixture was allowed to cool to room temperature and hot hexane (400 mL) was added. This mixture was then repeated washed by HCl (2N, 4×50 mL). The hexane was partially removed by evaporation, and the resultant solid was collected by filtration and re-crystallized from hexane to afford compound 70 (7.0 g, 60.6% yield). M.p. 111.0-113.3° C. $^1$H NMR (C$_6$D$_6$) δ 6.53 (s, 2H), 2.51 (t, 4H), 1.64 (m, 4H), 1.27 (m, 28H), 0.89 (t, 6H). $^{13}$C NMR: 141.26, 136.42, 133.17, 132.04, 120.73, 32.31, 30.03, 29.96, 29.90, 29.79, 29.66, 29.04, 23.07, 14.28.

Example 5

Figure 14:
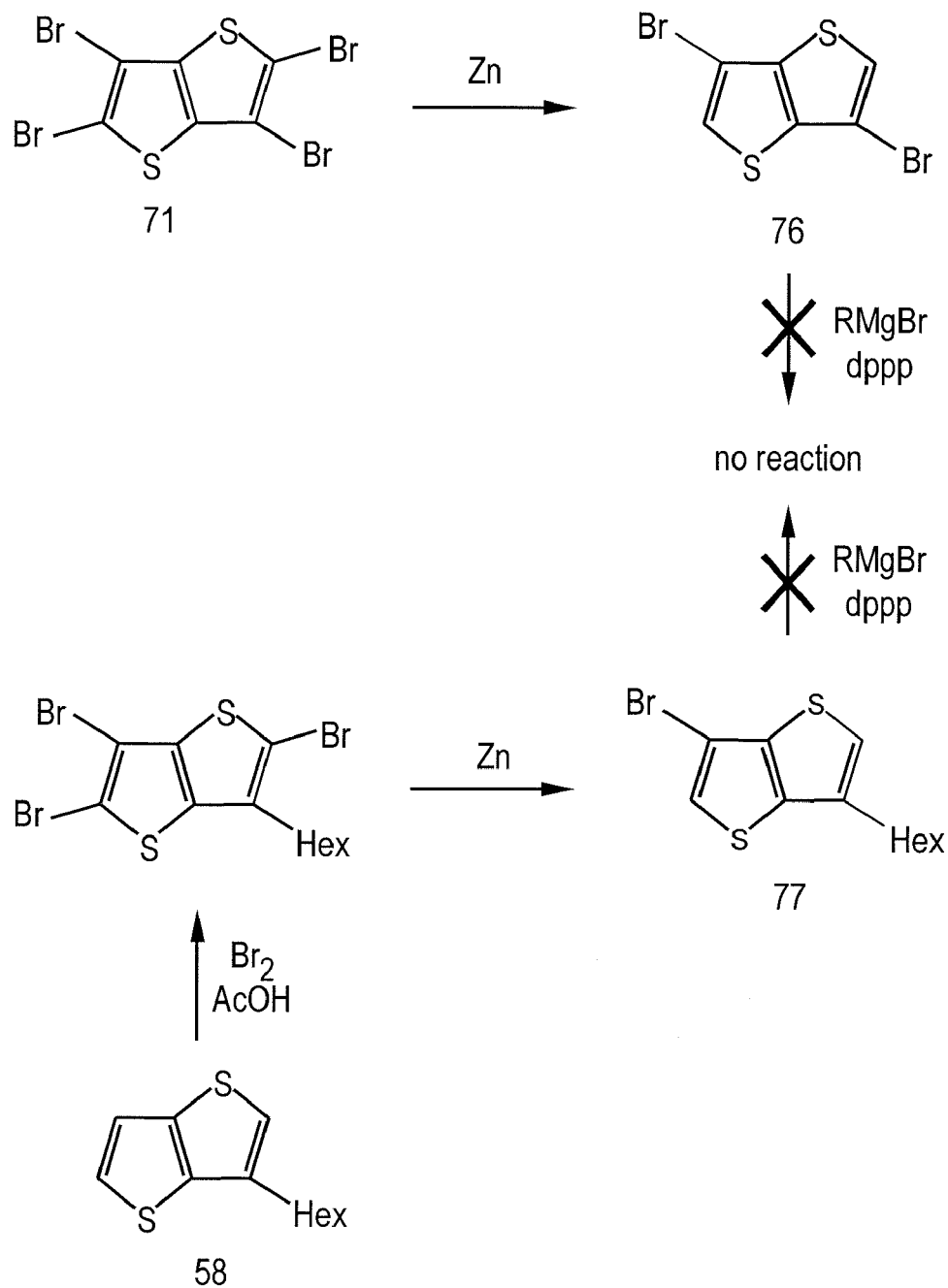
FIG. 14 is a reaction scheme showing the failed synthesis of β-hexyl-substituted thieno[2,3-d]thiophene according to conventional methodologies as described in Example 5.

Failed Attempt to Synthesize β-substituted thieno[2,3-d]thiophenes Using Conventional Coupling Reactions The reaction scheme of FIG. 14 was followed in an unsuccessful attempt to synthesize β-hexyl-substituted thieno[2,3-d]thiophene. Because the electronic properties of the fused ring systems are much different than those of a simple monocyclic thiophene, the coupling reactions used for the monocyclic thiophenes did not work.

3,6-dibromothieno[3,2-b]thiophene (76, 5.2 g, 0.0175 mol) was dissolved in dry diethyl ether (100 mL), and mixed with [1,3-bis(diphenylphosphino)propane]di-chloronickel (II) (dppp) (0.47 g, 0.05 equivalents). To this solution hexylmagnesium bromide (22.0 mL of 2.0 M solution in diethyl ether, 0.044 mol) was added dropwise. The resulting mixture was heated at reflux for 24 hours. The reaction was monitored by GC/MS. After 24 hours, the starting material had disappeared, but no Grignard adduct had been formed.

3-bromo-6-hexylthieno[3,2-b]thiophene (77, 6.2 g, 0.021 mol) was dissolved in dry diethyl ether (100 mL) and mixed with [1,3-bis(diphenylphosphino)propane]di-chloronickel (II) (dppp) (0.51 g, 0.05 equivalents). To this solution hexylmagnesium bromide (13.3 mL of 2.0 M solution in diethyl ether, 0.027 mol) was added dropwise.

The resulting mixture was heated at reflux for 24 hours. The reaction was monitored by GC/MS. After 6 hours, the starting material had disappeared, but no Grignard adduct had been formed.

Example 6

Poly(β-Substituted Fused Thiophenes)

Fused thiophene polymers were made using the general procedure described below. This procedure is adapted from Andersson et al., Macromolecules 1994, 27, 6506, which is incorporated herein by reference.

A monomeric α,α'-dihydro β,β'-dialkyl fused thiophene compound (10 mmol) was dissolved in 30 mL chlorobenzene. A suspension of ferric chloride (2.5 mmol) in 20 mL chlorobenzene was added to the monomer solution over half an hour. The mixture was allowed to stir for several (e.g. from 6 to 24) hours at room temperature. It may be desirable to heat the reaction mixture at 80-90° C. for several hours for fused thiophene compounds having larger (e.g. 4 or greater) numbers of rings in their fused ring system. The reaction mixture was then precipitated from 500 mL 95:5 methanol:water. The precipitate was collected by filtration, dissolved in toluene, boiled with concentrated ammonia (3×60 mL), and boiled with ethylenediaminetetraacetic acid (0.05 M in water, 2×50 mL). The organic layer was precipitated from methanol (500 mL); filtration and vacuum drying (70-80° C.) yielded polymeric material.

Poly(3,6-dihexylthieno[2,3-d]thiophene) (num, 35% yield); poly(3,6-didecylthieno[2,3-d]thiophene (num, 90% yield); poly(3,7-didecylthieno[3,2-b]thieno[2',3':4,5]thieno[2,3-d]thiophene) (num, 80% yield); and poly(3,5-didecyldithieno[3,2-b:2',3'-d]thiophene-4,4-dioxide) (num, 43% yield) were prepared.

Example 7

Synthesis 2-2, 3-3 and 4-4 Dimer and 5 and 7 Ring Systems

The synthesis 2-2, 3-3 and 4-4 dimers and 5 and 7 ring systems is depicted in FIG. 15.

3,3'-dibromo-6,6'-didecanyl-2,2'-bisthienothiophene (82). To a flask with diisopropylamine (4.0 g, 0.039 mol) in dry THF (30 mL), butyllithium (2.5 M in hexane, 15.6 mL, 0.039 mol) was added dropwise at 0° C. The resulting mixture was kept at 0° C. for 15 minutes. 3-bromo-6-decanylthienylhiophene (81) (14.0 g, 0.039 mol) was added dropwise as a THF solution (30 mL). This mixture was stirred at 0° C. for one hour before cupper (II) chloride (6.3 g, 0.047 mol) was added. This dark brown solution was stirred for an additional 12 hours at room temperature. After evaporation all of the solvent, the residue was boiled with toluene (200 mL), and the solid was filtered. The organic solution was washed by brine (2×50 mL), water (50 mL) and dried over MgSO$_4$. After the toluene was evaporated, the residue was boiled with ethanol (700 mL) and the solid was collected after cooling. The target compound was collected as a yellow solid crystal powder. Yielded 9.35 g (67%). Mp. 90.0-91.0° C. $^1$HNMR: solvent CD$_2$Cl$_2$. δ: 7.15 (s, 2H), 2.74 (t, 4H), 1.89-1.27 (m, 32H), 0.89 (t, 6H). $^{13}$CNMR: 140.78, 136.25, 133.02, 131.65, 131.23, 120.47, 31.92, 29.61 (overlap), 29.36 (overlap), 28.73, 22.69, 14.11.

3,6-didecanyl-dithieno[2,3-d:2',3'-d']thieno[3,2-b:4,5-b']dithiophene (83). 3,3'-dibromo-6,6'-didecanyl-2,2'-bisthienothiophene (82) (8.6 g, 0.012 mol) was dissolved into THF (100 mL). This solution was cooled to −78° C. under argon. To this solution, butyllithium (9.6 mL, 0.024 mol) was added dropwise, the resulting mixture was stirred for 30 minutes at −78° C. and bis(phenylsulfonyl)sulfide (3.8 g, 0.012 mol) was added. This solution was stirred overnight at room temperature before the THF was evaporated. The residue was dissolved into hexane (300 mL) and the organic layer was washed with brine (2×100 mL), water (50 mL). The organic layer then was dried over MgSO$_4$. After evaporating the solvent, the crude product was purified by column chromatography (hot hexane) to give solid compound. This yellow compound was recrystallized from hexane, yielded 3.2 g (45.3%). Mp. 107.7-108.5° C. $^1$HNMR: Solvent CD$_2$Cl$_2$. δ, 7.024 (s, 2H), 2.76 (t, 4H), 1.79-1.28 (m, 32H), 0.88 (t, 6H). $^{13}$CNMR: 140.58, 138.96, 135.94, 129.80, 122.86, 105.64, 31.92, 29.77, 29.57, 29.33 (overlap), 28.69, 22.69, 14.11.

Figure 15A:
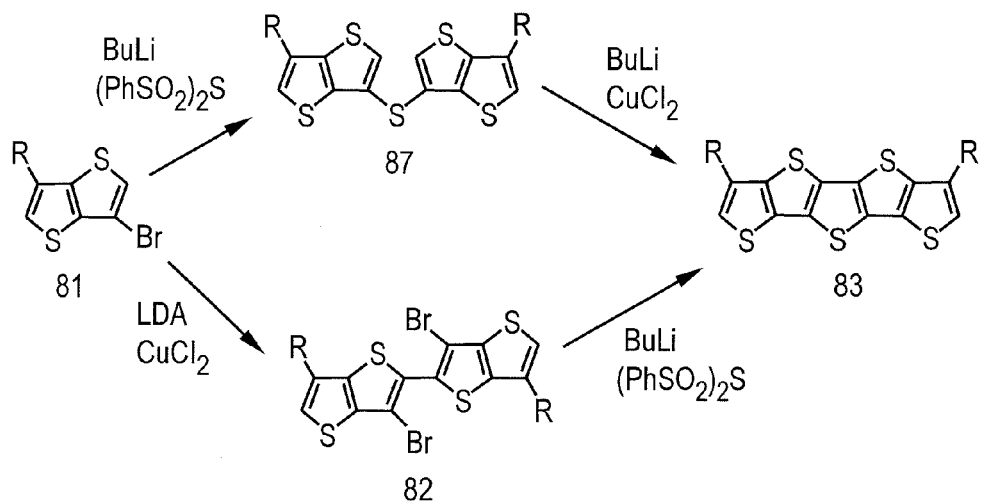
FIG. 15 is a reaction scheme for the synthesis 2-2, 3-3 and 4-4 dimers and 5- and 7-ring systems according to Example 7.

Referring to FIG. 15A, 83 can also be prepared by the cyclization of 87 with butyllithium and copper chloride.

3,3'-dibromo-5,5'-didedecanyl-2,2'-bisdithieno[3,2-b:2',3'-d]thiophene (85). To a flask with diisopropylamine (1.13 g, 0.011 mol) in dry THF (30 mL), butyllithium (2.5 M in hexane, 4.4 mL, 0.011 mol) was added dropwise at 0° C. The resulting mixture was kept at 0° C. for 15 minutes. 3-bromo-5-decanyl-dithieno[3,2-b:2',3'-d]thiophene (84) (4.61 g, 0.011 mol) was dissolved into THF (40 mL) and added dropwise. This mixture was stirred at 0° C. for one hour before cupper (II) chloride (1.77 g, 0.013 mol) was added. This dark green solution was stirred for an additional 12 hours at room temperature. After evaporating all of the solvent, the residue was boiled with toluene (2×100 mL) and the solid was filtered. After evaporating all of the toluene, the residue was boiled with toluene (200 mL) and cool to room temperature. Crystalline solid was collected after cooling. Yield 2.0 g. (43.8%). Mp. 140.2-141.1° C. $^1$HNMR: Solvent, CD$_2$Cl$_2$. $^1$HNMR: δ 7.11 (s, 2H), 2.78 (t, 4H), 1.75-1.28 (m, 32H), 0.86 (t, 6H).

3,7-didecanyl-bisdithieno{[3,2-b;4,5-d][2',3'b;4',5'-d]}thiophene (86). 3,3'-dibromo-5,5'-didecanyl-bisdithienothiophene (85) (3 g, 3.62 mmol) was dissolved in dry tetrahydrofuran (80 mL) and cooled to −78° C. To this mixture, butyllithium (7.23 mmol, 2.9 mL) was added dropwise under argon. This resulting mixture was stirred at −78° C. for one hour before bis(phenylsulfonyl)sulfide (1.15 g, 3.62 mmol) was added through a solid addition funnel. The resulting mixture was stirred and slowly warmed up to room temperature during overnight. After evaporating the THF, the residue was refluxed with water (200 mL) and filtrated. The solid was then washed by methanol (2×50 mL) and refluxed with toluene (200 mL). The hot toluene solution was filtered to remove undissolved solid. After evaporating the toluene, the solid was re-dissolved into toluene (70 mL) and cooled to room temperature to produce brown-yellow needles of the target compound (1.68 g, 66.3%). Mp. 140.2-141.1° C. $^1$HNMR solvent CD$_2$Cl$_2$ δ 7.11 (s, 2H), 2.78 (t, 4H), 1.79-1.28 (m, 32H), 0.88 (t, 6H).

Figure 15B:
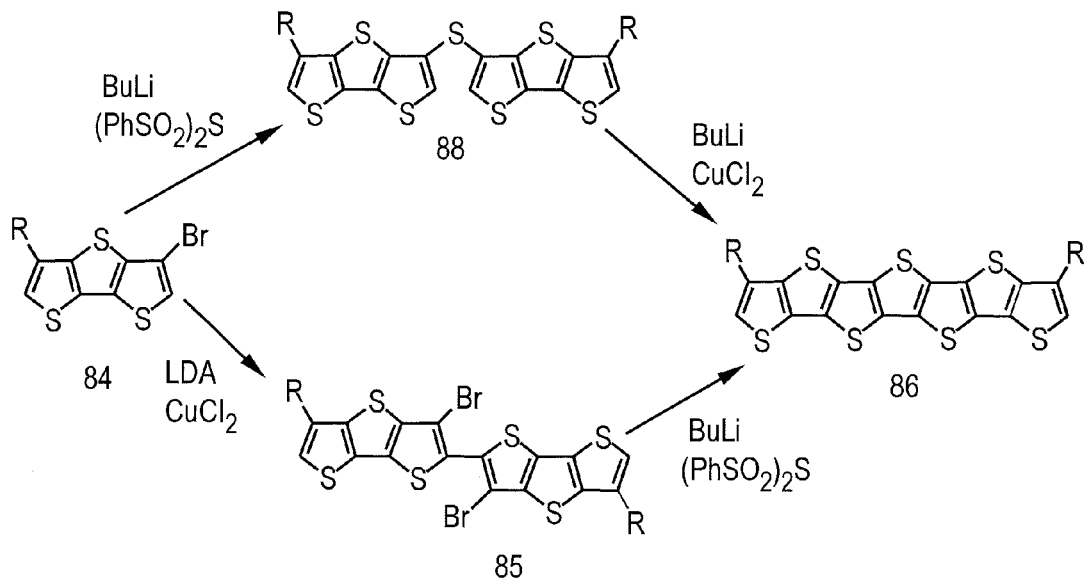

Referring to FIG. 15B, 86 can also be prepared by the cyclization of 88 with butyllithium and copper chloride.

Example 8

Synthesis of Tetraalkylsubstituted Thienothiophene Dimer

Figure 16:
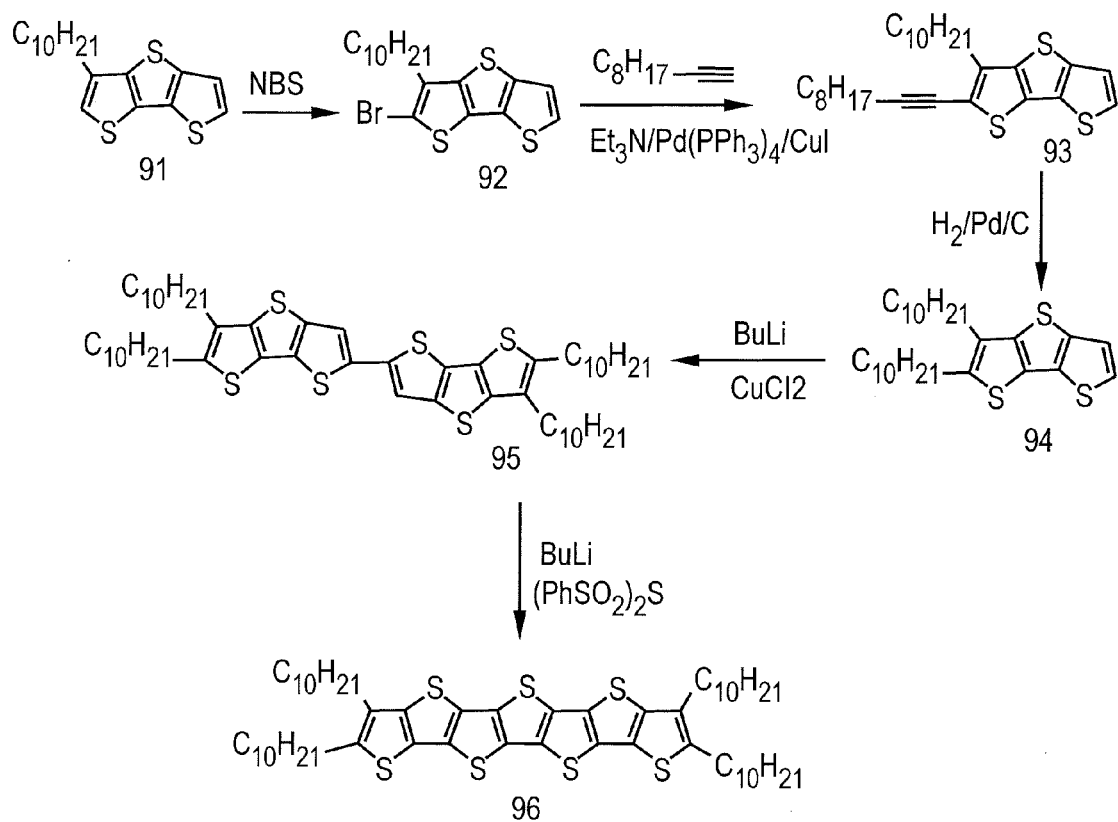
FIG. 16 is a reaction scheme for the synthesis of a three-ring tetraalkyl substituted thienothiophene according to Example 8.
Figure 17:
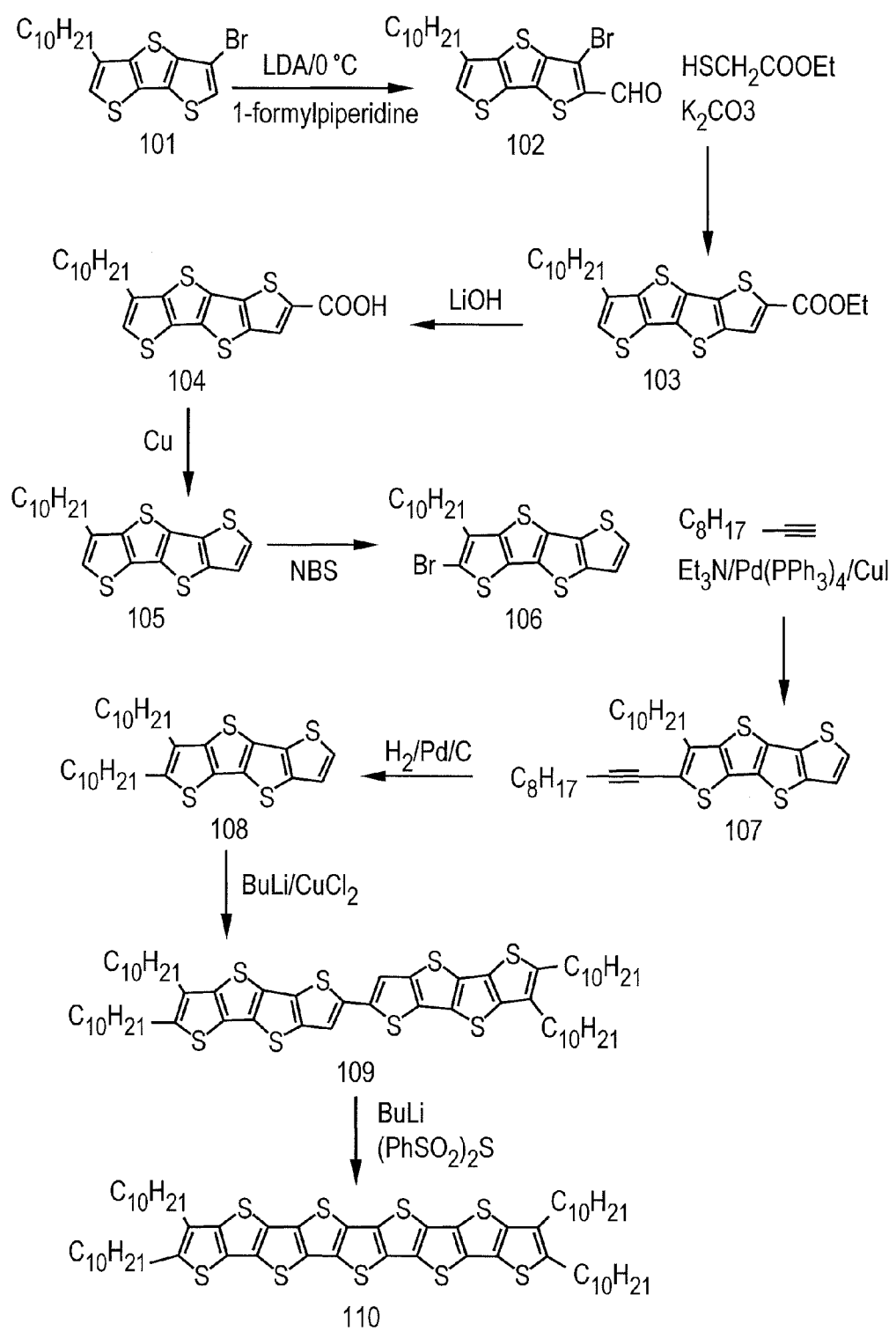
FIG. 17 is a reaction scheme for the synthesis of a four-ring tetraalkyl substituted thienothiophene according to Example 8.

The synthesis of three-ring and four-ring tetraalkylsubstituted thienothiophene dimers is depicted in FIGS. 16 and 17, respectively.

Three Ring Dimer 2-bromo-3-decanyldithieno[3,2-b:2',3'-d]thiophene (92). 3-decanyldithieno[3,2-b:2',3'-d]thiophene (91) (9.03 g, 0.027 mol) was dissolved in DMF (100 mL). To this solution, N-bromosuccinimide (NBS) (4.78 g, 0.027 mol) in DMF (50 mL) was added dropwise in the dark under argon. The resulting mixture was stirred at 0° C. for three hours. GC/MS showed a single peak at 415. This solution was poured into water (500 mL). Organic solution was extracted with hexane (3×100 mL). The combined organic solutions were washed with brine (2×50 mL) and water (50 mL). After drying over $MgSO_4$, the hexane was evaporated. The crude product was purified by column chromatography and eluted with hexane to yield the target compound (10.1 g, 90.2%). $^1$HNMR: solvent, $CD_2Cl_2$. δ 7.39 (d, 1H), 7.29 (d, 1H), 2.74 (t, 2H), 1.74-1.33 (m, 16H), 0.89 (t, 3H). $^{13}$CNMR: 140.89, 140.63, 136.00, 131.55, 129.22, 126.58, 121.04, 108.89, 32.31, 29.94, 29.73 (overlap), 29.35, 28.49, 23.09, 14.27.

3-decanyl-6-dec-1-ynyldithieno[3,2-b:2',3'-d]thiophene (93). 2-bromo-3-decanyldithieno[3,2-b:2',3'-d]thiophene (92) (4.16 g, 0.01 mol) was mixed with 1-decyne (3.6 g, 0.026 mol), tetrakis(triphenylphosphine)palladium (0.58 g, 0.5 mmol) and copper(I) iodide (0.19 g, 1.0 mmol) in triethylamine (80 mL). This mixture was bubbled with nitrogen for 5 minutes and then heated up to 130° C. under argon for 16 hours. Triethylamine was evaporated and hexane (150 mL) was added. This mixture was filtered to remove solid salts. The organic layer was washed with 1 M hydrochloric acid (50 mL) and brine (50 mL) then dried over $MgSO_4$. The solvent was removed in vacuo, and the residue was purified by chromatography on silica gel eluting with hexane to yield the target compound (3.87 g, 93.0%). $^1$HNMR, solvent $CD_2Cl_2$. δ 7.36 (d, 1H), 7.30 (d, 1H), 2.82 (t, 2H), 2.49 (t, 2H), 1.63-1.27 (m, 28H), 0.88 (m, 6H).

2,3-didecanyldithieno[3,2-b:2',3'-d]thiophene (94). 3-decanyl-6-dec-1-ynyldithieno[3,2-b:2',3'-d]thiophene (93) (36.0 g, 0.076 mol) was dissolved into ethyl acetate (60 mL). To this solution, 5% Pt/C (9.0 g) was added. The mixture was stirred under a $H_2$ atmosphere (90 psi) for 24 hours. The solution was then filtered. After removal of the ethyl acetate, the residue was purified by chromatography on silica gel eluted with hexane to produce the target compound (29.0 g, 79.9%). $^1$HNMR: solvent, $CD_2Cl_2$ δ 7.29 (d, 1H), 7.27 (d, 1H), 2.80 (t, 2H), 2.67 (t, 2H), 1.68-1.27 (m, 32H), 0.88 (m, 6H). $^{13}$CNMR. 142.88, 140.75, 139.82, 131.69, 131.37, 126.69, 125.04, 120.94, 32.16, 29.85 (m, overlap), 22.93, 14.11.

5,6,5'6'-tatradecanyl-2,2'-bisdithieno[3,2-b:2',3'-d]thiophene (95). To a hexane solution of 2,3-didecanyldithieno[3,2-b:2',3'-d]thiophene (94) (5.16 g, 0.011 mol) and N,N,N',N'-tetramethylethylenediamine (TMEDA) (1.25 g, 0.011 mol), butyllithium (4.5 mL, 0.011 mol) was added dropwise under argon at room temperature. The resulting mixture was refluxed for one hour before copper (II) chloride powder was added to the reaction. This mixture was stirred overnight and hexane was removed in vacuo. The residue was boiled with toluene (80 mL) and the solid residue was removed by filtration. The organic layer was washed with brine (2×30 mL) and water (30 mL) and dried over $MgSO_4$. After removal of the toluene, the yellow solid was boiled with acetone (400 mL) and cooled to room temperature to produce crystalline target compound (1.26 g, 24.5%). $^1$HNMR: Solvent $CD_2Cl_2$. δ 7.43 (s, 2H), 2.89 (t, 4H), 2.73 (t, 4H), 1.76-1.34 (m, 64H), 0.93 (m, 12H). $^{13}$CNMR: solvent $C_6D_{12}$. 143.28, 141.09, 140.94, 138.12, 131.66, 131.41, 127.91, 117.18, 32.74, 32.63, 30.44, 30.39, 30.32, 30.29, 30.13, 29.86, 28.58, 23.41, 14.25.

Referring to FIG. 16, 96 can also be prepared by the cyclization of 95 with butyllithium and bis(phenylsulfonyl) sulfide.

Four Ring Dimer

2-Formyl-3-bromo-5decanyldithieno[3,2-b:2',3'-d]thiophene (102). To a flask with diisopropylamine (2.76 g, 0.027 mol) in dry THF (100 mL), butyllithium (2.5 M in hexane, 10.9 mL, 0.0273 mol) was added dropwise at 0° C. The resulting mixture was kept at 0° C. for 15 minutes. 3-bromo-5-decanyl-dithieno[3,2-b:2',3'-d]thiophene (101) (11.33 g, 0.0273 mol) was dissolved into THF (60 mL) and added dropwise to the reaction. This mixture was kept at 0° C. for one hour before 1-formylpiperidine was added. The resulting mixture was stirred overnight and THF was removed. The residue was washed with 10% hydrochloric acid (30 mL) and water (3×100 mL). The solid target compound was purified by crystallization from ethyl alcohol (100 mL). Yield 8.80 g (72.8%). Mp. 65.5-67.2° C.

2-carboxylic ethyl ester-5decanyldithieno[2,3-d:2',3'-d']thieno[3,2-b:4,5-b']dithiophene (103). 2-Formyl-3-bromo-5-decanyldithieno[3,2-b:2',3'-d]thiophene (102) (8.80 g, 0.02 mol) was dissolved into DMF (100 mL) and mixed with potassium carbonate (9.66 g, 0.07 mol). A catalytic amount 18-crown-6 ether was used as catalyst. To this solution, ethyl thioglycolate (2.52 g, 0.021 mol) was added dropwise at 60-70° C. This mixture was stirred at this temperature overnight. After checking the GC/MS, the mixture was poured into water (500 mL). The solid formed from the water solution was removed by filtration. The solid was then washed with water (2×200 mL) and methanol (200 mL). GC/MS showed a single peak at 465. After drying in vacuo, the target compound was used without further purification. (8.0 g, 86%). Mp. 59.4-62.0° C.

2-carboxylic acid-5-decanyldithieno[2,3-d:2',3'-d']thieno[3,2-b:4,5-b']dithiophene (104). 2-carboxylic ethyl ester-3-bromo-5decanyldithieno[2,3-d:2',3'-d']thieno[3,2-b:4,5-b']dithiophene (103) (9.3 g, 0.02 mol) was dissolved in THF (100 mL). To this solution, methanol (20 mL) was added. LiOH (10% solution, 7 mL) was also added to this mixture. A catalytic amount of tetrabutylammonium iodide was used as catalyst. This mixture was refluxed overnight. After removal ⅔ of the solvent, the residue was poured into concentrated HCl (100 mL). The solid was collected by filtration and washed with water until neutral. After drying, 6.06 grams of target compound was obtained (yield 69.3%). Mp. 225-227° C.

5-decanyldithieno[2,3-d:2',3'-d']thieno[3,2-b:4,5-b']dithiophene (105). 2-carboxylic acid-5-decanyldithieno[2,3-d:2',3'-d']thieno[3,2-b:4,5-b']dithiophene (104) (6.06 g, 0.014 mol) was dissolved into quinoline (80 mL). Copper chloride powder (0.62 g, 9.7 mmol) was also added to this mixture. The mixture was heated to 240-260° C. until no gas bubbles were observed (about one hour). The mixture was cooled to room temperature and poured into 30% HCl water solution (300 mL). The organic solution was extracted with hexane (150 mL) and washed with 10% HCl several times until quinoline was removed from the organic layer. The organic layer was then dried over $MgSO_4$. After removing the solvent, the residue was recrystallized from ethanol to produce 4.44 g of target compound (yield 81.3%). Mp. 88.3-89.6° C. $^1$HNMR. Solvent $CD_2Cl_2$. δ 7.38 (d, 1H), 7.32 (d, 1H), 6.99 (m, 1H), 2.73 (t, 2H), 1.77 (m, 2H), 1.35-1.27 (m, 14H), 0.87 (t, 3H). $^{13}$CNMR: 141.29, 140.59, 136.72, 133.51, 132.32, 132.27, 131.51, 126.29, 121.15, 121.02, 32.32, 30.00, 29.96, 29.78 (overlap), 29.73, 29.11, 23.09, 14.28.

2-Bromo-3-decanyldithieno[2,3-d:2',3'-d']thieno[3,2-b:4,5-b']dithiophene (106). To 5-decanyldithieno[2,3-d:2',3'-d']thieno[3,2-b:4,5-b']dithiophene (105) (5.56 g, 0.0113 mol) in dry DMF (50 mL), NBS (2.01 g, 0.0113 mol) in DMF (30 mL) was added dropwise in the dark at 0° C. The resulting mixture was stirred for two hours and poured into water (500 mL). The solid was filtered and washed by water several times. Ethanol (200 mL) was used to recrystallize the crude compound to give 5.06 g (94.9%). Mp. $^1$HNMR: Solvent $CD_2Cl_2$. δ 7.43 (d, 1H), 7.34 (d, 1H), 2.77 (t, 2H), 1.74 (m, 2H), 1.36-1.27 (m, 16H), 0.87 (t, 3H). $^{13}$CNMR: 140.87, 139.54, 135.98, 133.31, 132.11, 131.70, 130.26, 126.77, 121.23, 109.03, 32.32, 29.99, 29.92, 29.75, 29.66, 29.36, 28.50, 23.09, 14.28.

2-dec-1-ynyl-3-decanyldithieno[2,3-d:2',3'-d']thieno[3,2-b:4,5-b']dithiophene (107). 2-Bromo-3-decanyldithieno[2,3-d:2',3'-d']thieno[3,2-b:4,5-b']dithiophene (2.16 g, 4.6 mmol) (106) was mixed with 1-decyne (1.27 g, 9.2 mmolmol), tetrakis(triphenylphosphine)palladium (0.27 g, 0.23 mmol) and copper(I) iodide (0.087 g, 0.46 mmol) in triethylamine (50 mL). This mixture was bubbled with nitrogen for 5 minutes and then heated up to 130° C. under argon for 16 hours. The triethylamine was evaporated and hexane (150 mL) was added. This mixture was filtered to remove solid salts. The organic layer was washed with 1 M hydrochloric acid (50 mL) and brine (50 mL), then dried over $MgSO_4$. The solvent was removed in vacuo, and the residue was purified by chromatography on silica gel eluted with hexane to produce the target compound (2.3 g, 90.2%). $^1$HNMR: Solvent $CD_2Cl_2$. δ 7.41 (d, 1H), 7.33 (d, 1H), 2.84 (t, 2H), 2.23 (t, 2H), 1.73-1.27 (m, 28H), 0.89 (m, 6H).

2,3-didecanyldithieno[2,3-d:2',3'-d']thieno[3,2-b:4,5-b']dithiophene (108). 2-dec-1-ynyl-3-decanyldithieno[2,3-d:2',3'-d']thieno[3,2-b:4,5-b']dithiophene (107) (2.2 g, 4.15 mmol) was dissolved into ethyl acetate (30 mL). To this solution, 5% Pt/C (0.5 g) was added. The mixture was stirred under a $H_2$ atmosphere (90 psi) for 24 hours. The solution was then filtered. After removal of the ethyl acetate, the residue was purified by chromatography on silica gel eluted with hexane to produce the target compound (2.00, 90.5%). Mp. 50.9-52.5° C. $^1$HNMR: solvent, $CD_2Cl_2$ δ 7.41 (d, 1H), 7.33 (d, 1H), 2.83 (t, 2H), 2.50 (t, 2H), 1.73-1.26 (m, 32H), 0.87 (m, 6H). $^{13}$CNMR: 140.85, 140.40, 139.93, 133.38, 133.14, 132.22, 129.69, 121.17, 120.09, 98.92, 32.29, 32.25, 29.99, 29.94, 29.72, 29.63, 29.52, 29.33, 29.18, 29.06, 28.94, 23.05, 14.23.

Referring to FIG. 17, 109 can be prepared by coupling 108 with butyllithium and copper chloride. The cyclization of 109 to produce 110 can be accomplished by reacting 109 with butyllithium and bis(phenylsulfonyl)sulfide.

Example 9

Synthesis of Polymers Containing Fused Thiophene Moiety

Poly-3,6-dihexyl-thieno[3,2-b]thiophene (PDC6FT2) and Poly-3,6-didecanyl-thieno[3,2-b]thiophene (PDC10FT2). The monomer, 3,6-dihexyl-thieno[3,2-b]thiophene (3.08 g, 0.01 mol) was dissolved into chlorobenzene. A suspension of $FeCl_3$ in chlorobenzene was added to the monomer solution within a half hour. The final concentration for the monomer and $FeCl_3$ was 0.05 and 0.2 M, respectively. The mixture was stirred for 6-24 hours at room temperature. For larger ring sizes, the mixture can be heated to 80-90° C. for several hours. The polymer solution was poured into 5% water methanol solution and a precipitate formed. The polymer was collected through filtration and re-dissolved into toluene. The toluene solution then was boiled with concentrated ammonia (3×60 mL) and then boiled twice with ethylenediaminetetraacetic acid (EDTA) (0.05 M in water) (2×50 mL). The resulting toluene was slowly dropwise to methanol (500 mL) to precipitate polymer. After filtration, the polymer was dried in vacuum oven (70-80° C.) overnight. Yields of PDC6FT2 and PDC10FT2 were 35% and 90%, respectively.

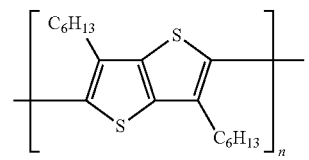

PDC6FT2

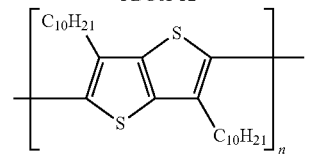

PDC10FT2

The method above was also used to produce the polymers PDC10FT2 (80% yield) and PDC10FTS3 (43% yield)

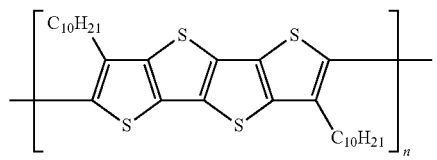

PDC10FT2

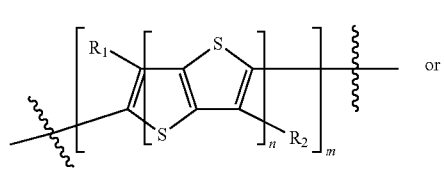

PDC10FTS3

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:
1. A composition comprising at least one fused thiophene moiety comprising the formula 3 or 4

-continued

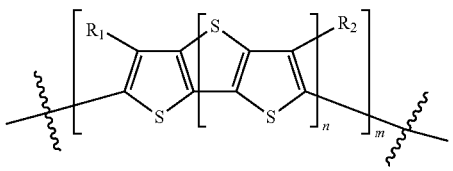

wherein n is an integer greater than two; m is no less than one; $R_1$ and $R_2$ are, independently, hydrogen or an alkyl group, wherein at least one of $R_1$ and $R_2$ is an alkyl group.

2. The composition of claim 1, wherein both $R_1$ and $R_2$ are an alkyl group comprising at least four carbon atoms.

3. The composition of claim 2, wherein $R_1$ and $R_2$ are the same or different alkyl group.

4. The composition of claim 1, wherein n is from 3 to 15.

5. The composition of claim 1, wherein n is 3 or 4.

6. The composition of claim 1, wherein m is at least 4.

7. A monomer, oligomer, or polymer comprising the fused thiophene moiety of claim 1.

8. The polymer of claim 7, wherein the polymer comprises a homopolymer comprising as the repeat unit the fused thiophene moiety.

9. The polymer of claim 7, wherein polymer comprises the fused thiophene moiety incorporated in a polymer comprising a polyester, a polyurethane, a polyamide, a polyketone, a polyacrylate, a polymethacrylate, or a poly(vinyl ether).

10. The polymer of claim 7, wherein the polymer comprises a copolymer comprising the fused thiophene moiety conjugated with an aromatic or unsaturated moiety.

11. The polymer of claim 7, wherein the polymer comprises a copolymer comprising the polymerization product between the fused thiophene moiety and a substituted or unsubstituted thiophene.

12. A device comprising the composition of claim 1 configured in an electronic, optoelectronic, or nonlinear optical device.

* * * * *